(12) United States Patent
Coburn et al.

(10) Patent No.: US 7,109,217 B2
(45) Date of Patent: Sep. 19, 2006

(54) PHENYLCARBOXAMIDE BETA-SECRETASE INHIBITORS FOR THE TREATMENT OF ALZHEIMER'S DISEASE

(75) Inventors: Craig A. Coburn, Royersford, PA (US); Shawn J. Stachel, Perkasie, PA (US); Joseph P. Vacca, Telford, PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 10/534,291

(22) PCT Filed: Nov. 6, 2003

(86) PCT No.: PCT/US03/35316

§ 371 (c)(1),
(2), (4) Date: May 9, 2005

(87) PCT Pub. No.: WO2004/043916

PCT Pub. Date: May 27, 2004

(65) Prior Publication Data

US 2006/0052615 A1    Mar. 9, 2006

Related U.S. Application Data

(60) Provisional application No. 60/425,560, filed on Nov. 12, 2002, provisional application No. 60/425,555, filed on Nov. 12, 2002.

(51) Int. Cl.
*A01N 43/40* (2006.01)
*A01N 43/36* (2006.01)
*C07D 211/44* (2006.01)
*C07D 207/08* (2006.01)

(52) U.S. Cl. ............... 514/327; 514/408; 546/194; 546/216; 546/242; 548/567; 548/570; 564/84; 564/86; 564/88

(58) Field of Classification Search .......... 514/335, 514/315, 408, 327; 546/242, 217, 194; 548/567, 548/571, 570

See application file for complete search history.

(56) References Cited

U.S. PATENT DOCUMENTS

| | | | |
|---|---|---|---|
| 5,585,397 A | 12/1996 | Tung et al. | |
| 5,780,498 A | 7/1998 | Saika et al. | |
| 5,783,701 A | 7/1998 | Tung et al. | |
| 5,847,109 A | 12/1998 | Garti et al. | |
| 5,986,102 A | 11/1999 | Dolle, III et al. | |
| 6,103,720 A | 8/2000 | Lubisch et al. | |
| 6,117,639 A | 9/2000 | Germann et al. | |
| 6,482,832 B1 | 11/2002 | Lubisch et al. | |
| 6,562,783 B1 | 5/2003 | Qiao et al. | |
| 6,562,827 B1 | 5/2003 | Lubisch et al. | |
| 6,610,734 B1 | 8/2003 | Kreft et al. | |
| 6,660,741 B1 | 12/2003 | Bornmann et al. | |
| 6,706,742 B1 | 3/2004 | De Nanteuil et al. | |
| 6,753,327 B1 | 6/2004 | Lubisch et al. | |
| 2001/0029563 A1 | 10/2001 | Campanale et al. | |
| 2003/0073217 A1 | 4/2003 | Barr et al. | |
| 2003/0171291 A1 | 9/2003 | Christie et al. | |

FOREIGN PATENT DOCUMENTS

| | | |
|---|---|---|
| CA | 2328720 | 10/1999 |
| DE | 196 50 975 | 6/1998 |
| DE | 198 17 461 | 10/1999 |
| DE | 198 18 614 | 10/1999 |
| WO | WO 96/22275 | 7/1996 |
| WO | WO 01/70672 | 9/2001 |
| WO | WO 02/02505 | 1/2002 |
| WO | WO 02/02506 | 1/2002 |
| WO | WO 02/02518 | 1/2002 |
| WO | WO 02/002518 | 1/2002 |
| WO | WO 02/002520 | 1/2002 |
| WO | WO 02/02520 | 1/2002 |

OTHER PUBLICATIONS

Moore et al., "Difluoro Ketone Peptidomimetics Suggest a Large S1 Pocket for Alzheimer's gamma-Secretase: Implications for Inhibitor Design," J. Med. Chem., vol. 43, pp. 3434-3442 (2000).

(Continued)

*Primary Examiner*—Kamal A. Saeed
*Assistant Examiner*—Yong Chu
(74) *Attorney, Agent, or Firm*—John C. Todaro; Melvin Winokur

(57) ABSTRACT

Disclosed are compounds of formula (I)

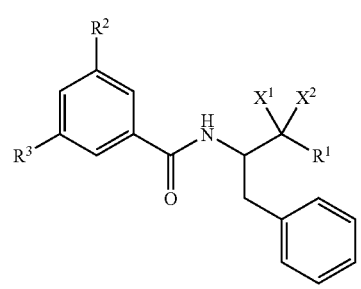

which are inhibitors of the beta-secretase enzyme and that are useful in the treatment or prevention of diseases in which the beta-secretase enzyme is involved, such as Alzheimer's disease and pharmaceutical compositions comprising these compounds and the use of these compounds and compositions in the prevention or treatment of such diseases in which the beta-secretase enzyme is involved.

10 Claims, No Drawings

OTHER PUBLICATIONS

Shearman et al., "L-685,458, an Aspartyl Protease Transition State Mimic, Is a Potent Inhibitor of Amyloid beta-Protein Precursor gamma-Secretase Activity," Biochemistry, vol. 39, pp. 8698-8704 (2000).

Li et al., "Photoactivated gamma-secretase inhibitors directed to the active site covalently label presenilin 1," Letter to Nature, vol. 405, pp. 689-694 (2000).

Barrish et al., "Aminodiol HIV Protease Inhibitors. 1. Design, Synthesis, and Preliminary SAR," J. Med. Chem., vol. 37, pp. 1758-1768 (1994).

PHENYLCARBOXAMIDE BETA-SECRETASE INHIBITORS FOR THE TREATMENT OF ALZHEIMER'S DISEASE

CROSS REFERENCE TO RELATED APPLICATIONS

This application is a U.S. National Phase application under 35 U.S.C. § 371 of PCT Application No. PCT/US03/353 16, filed Nov. 6, 2003, which claims priority under 35 U.S.C. § 119(e) from U.S. Provisional Application Ser. Nos. 60/425,555, filed Nov. 12, 2002 and 60/425,560, filed Nov. 12, 2002.

FIELD OF THE INVENTION

The present invention relates to phenylcarboxamide compounds that are useful for the prevention and treatment of Alzheimer's disease. More particularly, the present phenylcarboxamide compounds are useful inhibitors of β-secretase, the β-site amyloid precursor protein-cleaving enzyme ("BACE").

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production Aβ, and accumulation of β amyloid plaques in the brain, which is characteristic of Alzheimer's disease (see R. N. Rosenberg, Arch. Neurol., vol. 59, September 2002, pp. 1367–1368; H. Fukumoto et al, Arch. Neurol., vol. 59, September 2002, pp. 1381–1389; J. T. Huse et al, J. Biol. Chem., vol 277, No. 18, issue of May 3, 2002, pp. 16278–16284; K. C. Chen and W. J. Howe, Biochem. Biophys. Res. Comm, vol. 292, pp 702–708, 2002). Therefore, therapeutic agents that can inhibit β-secretase or BACE may be useful for the treatment of Alzheimer's disease.

The compounds of the present invention are useful for treating Alzheimer's disease by inhibiting the activity of the β-secretase or BACE, thus preventing the formation of insoluble Aβ and arresting the production of Aβ.

SUMMARY OF THE INVENTION

The present invention is directed to compounds that are inhibitors of the β-secretase enzyme that are useful in the treatment or prevention of diseases in which the β-secretase enzyme is involved, such as Alzheimer's disease. The invention is also directed to pharmaceutical compositions comprising these compounds and the use of these compounds and compositions in the prevention or treatment of such diseases in which the β-secretase enzyme is involved.

DETAILED DESCRIPTION OF THE INVENTION

The present invention is directed to compounds of the formula I:

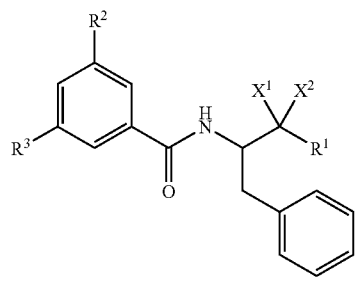

wherein:
$R^1$ is selected from the group consisting of:

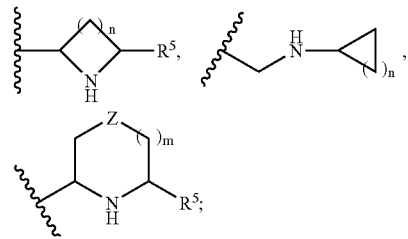

$R^2$ is selected from the group consisting of:
(1) $R^4$—$S(O)_m$—$NR^5$—,
(2) $R^4$—$S(O)_m$—,
(3) $R^4NHCO$—,
(4) $R^4CONH$—,
(5) $R^4R^5N$—,
(6) nitrile,
(7) NC—$C_{1-6}$alkyl-,
(8) halogen,
(9)

(10)

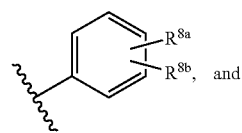
and

-continued

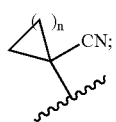

$R^3$ is selected from the group consisting of:

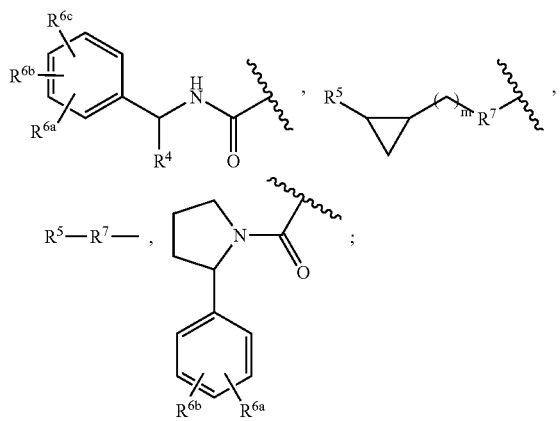

$R^4$ is selected from the group consisting of:
(1) hydrogen,
(2) $C_{1-6}$alkyl,
(3) phenyl, and
(4) benzyl;

$R^5$ is independently selected from the group consisting of:
(1) hydrogen,
(2) $C_{1-6}$alkyl,
(3) phenyl, and
(4) benzyl;

$R^{6a}$, $R^{6b}$, and $R^{6c}$ are independently selected from the group consisting of:
(1) hydrogen,
(2) halogen,
(3) —$OR^5$,
(4) —$SR^5$, and
(5) $C_{1-6}$alkyl;

$R^7$ is selected from the group consisting of —C≡C—, O, S, and NH;

Z is selected from the group consisting of CO, CH—OH, CH—F and

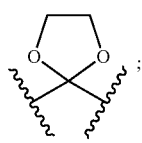

$R^{8a}$ and $R_{8b}$ are independently selected from the group consisting of:
(1) nitrile
(2) hydrogen,
(3) halogen,
(4) —$OR^5$,
(5) —$SR^5$,
(6) $C_{1-6}$alkyl,
(7) —$CO_2R_5$, and (8) tetrazolyl;

$X^1$ is hydrogen and $X^2$ is hydroxyl, or $X^1$ and $X^2$ together form oxo;

n is independently 1, 2, 3, or 4;

m is independently 0, 1, or 2;

and pharmaceutically acceptable salts thereof.

An embodiment of the present invention includes compounds of the formula IA wherein $X^1$ and $X^2$ of formula I together form oxo:

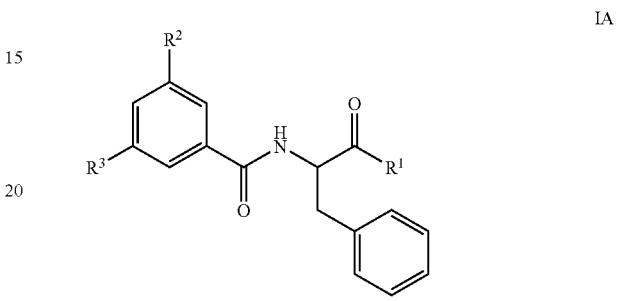

IA

Another embodiment of the present invention includes compounds of the formula IB wherein $X^1$ of formula I is hydrogen and $X^2$ of formula I is hydroxyl:

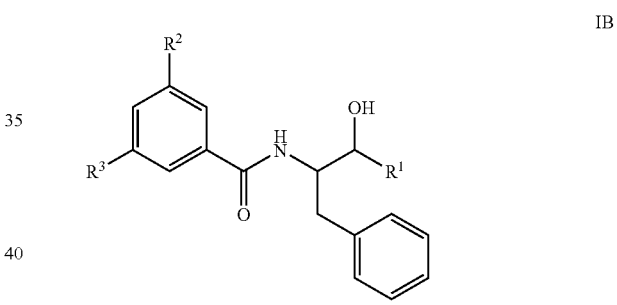

IB

An embodiment of the present invention includes compounds of the formula I wherein $R^1$ is:

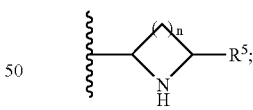

and wherein n is 2 or 3, $R^5$ is hydrogen or methyl, and pharmaceutically acceptable salts thereof.

Another embodiment of the present invention includes compounds of the formula I wherein $R^1$ is:

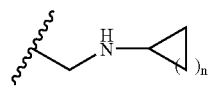

and wherein n is 1, and pharmaceutically acceptable salts thereof.

Another embodiment of the present invention includes compounds of the formula I wherein $R^1$ is:

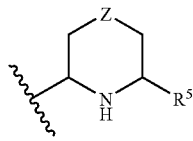

and wherein $R^5$ is hydrogen or methyl and Z is selected from the group consisting of CO, CH—OH, and

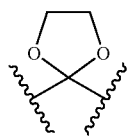

and pharmaceutically acceptable salts thereof.

Another embodiment of the present invention includes compounds of the formula I wherein $R^2$ is:

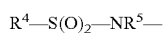

and wherein $R^4$ is selected from the group consisting of:
 (1) hydrogen,
 (2) $C_{1-6}$alkyl,
 (3) phenyl, and
 (4) benzyl;

$R^5$ is selected from the group consisting of:
 (1) $C_{1-6}$alkyl,
 (2) phenyl,
 (3) benzyl, and
 (4) hydrogen;

and pharmaceutically acceptable salts thereof.

Another embodiment of the present invention includes compounds of the formula I wherein $R^3$ is:

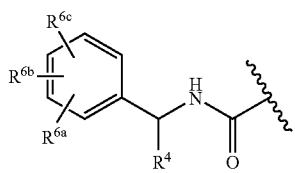

and wherein $R^4$ is methyl, $R^{6a}$ is H or F, $R^{6b}$ and $R^{6c}$ are hydrogen, and pharmaceutically acceptable salts thereof.

Another embodiment of the present invention includes compounds of the formula I wherein $R^3$ is:

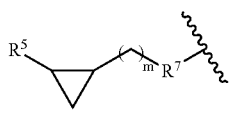

and wherein $R^5$ is methyl, $R^7$ is O or NH, and pharmaceutically acceptable salts thereof.

Another embodiment of the present invention includes a compound of formula IA which is selected from the group consisting of:

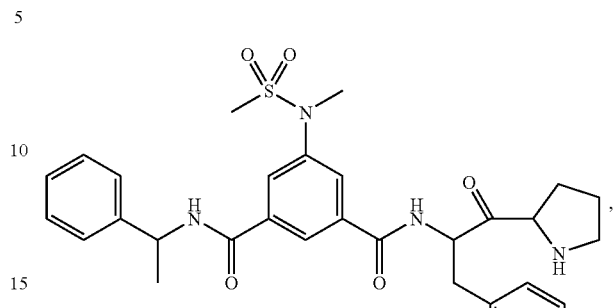

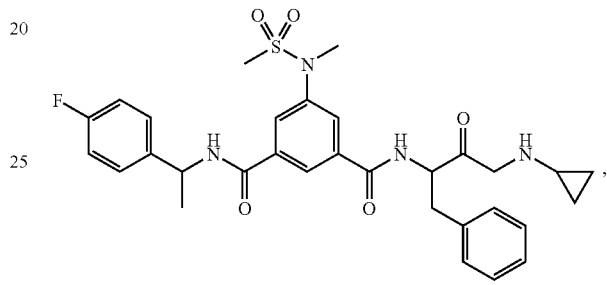

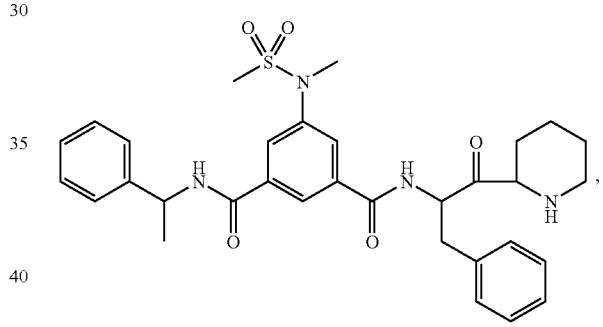

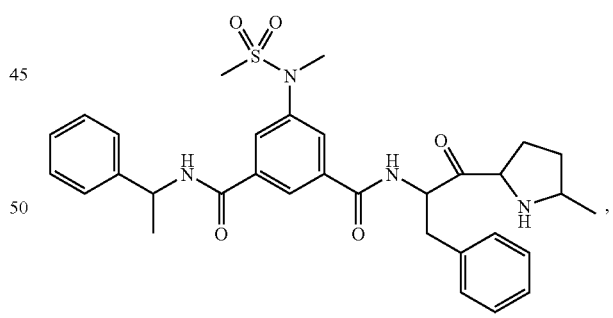

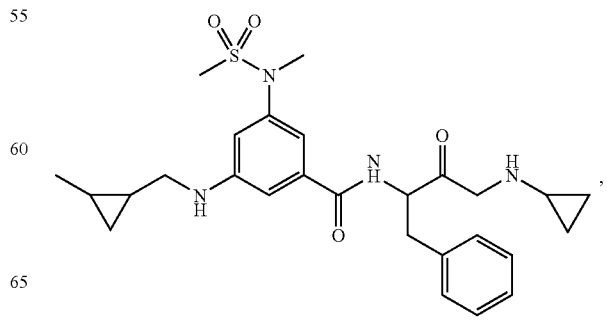

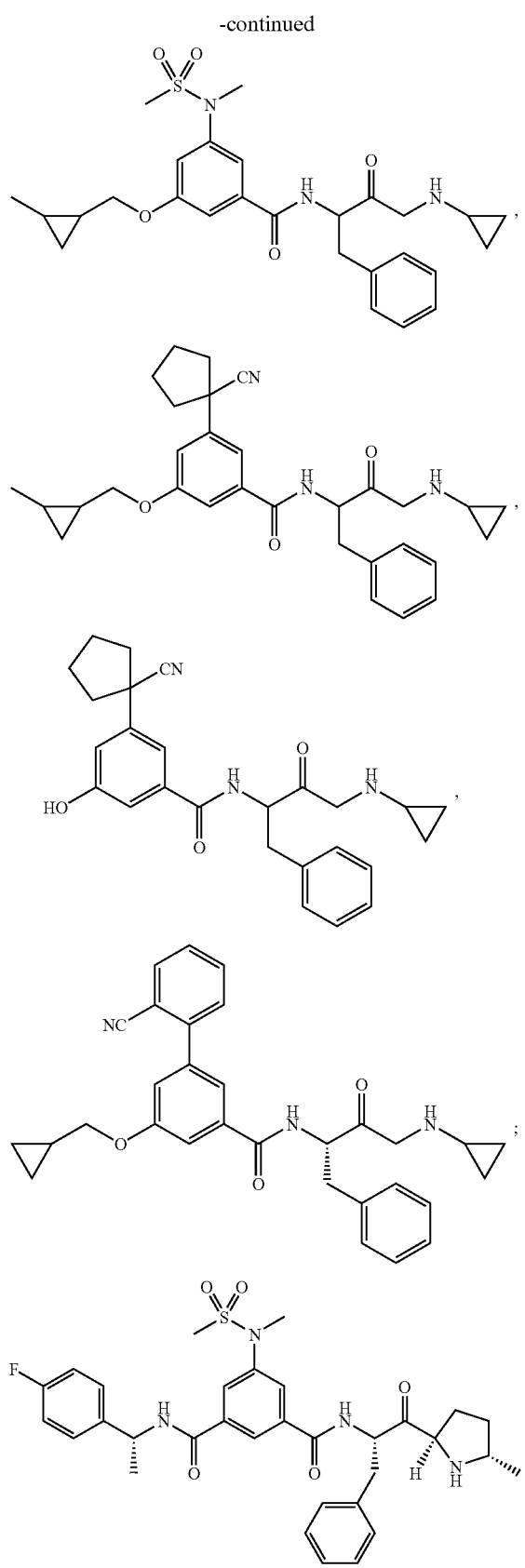
Another embodiment of the present invention includes a compound of formula IB which is selected from the group consisting of:

-continued

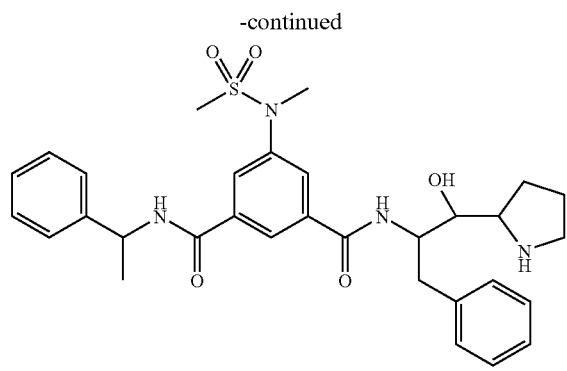

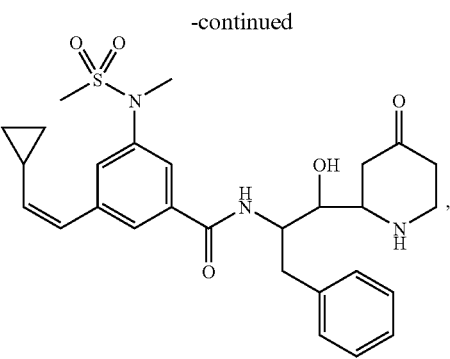

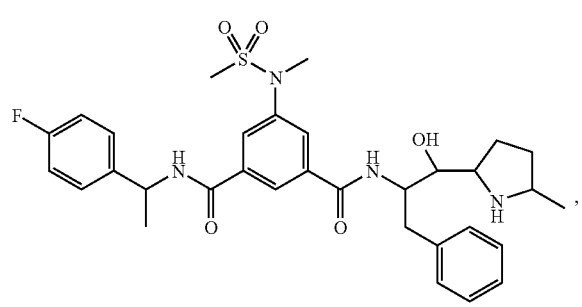

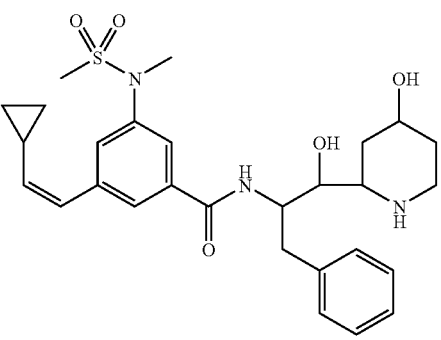

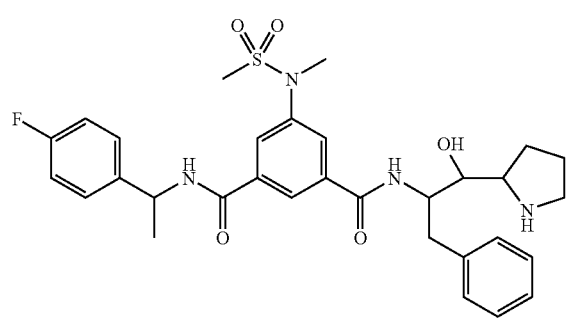

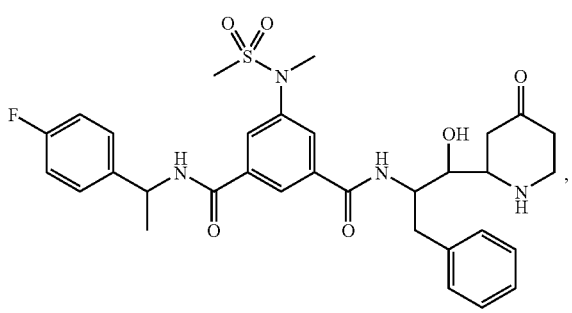

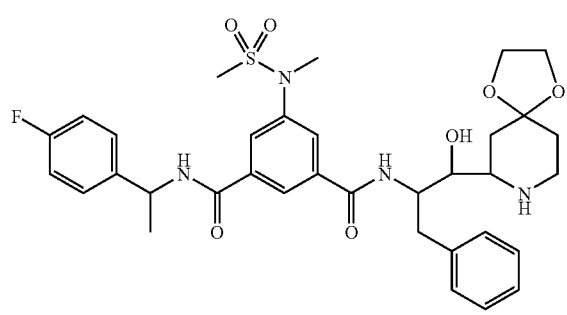

and pharmaceutically acceptable salts thereof.

Several documents disclose compounds that may be relevant to the phenylcarboxamide compounds of the present invention, for example WO99/61423 (Derwent 2000-097099), WO99/54305 (Derwent 2000-052697), WO99/54320 (Derwent 2000-023164), WO99/54310 (Derwent 2000-023162), DE19818614 (Derwent 2000–000334), DE19817461 (Derwent 1999-591908), WO98/25883 (Derwent 98-348419), DE19650975 (Derwent 98-323649), WO95/12611 Derwent 95-185737), WO96/22275, WO02/002505, US 2002/0128255 and US 2002/0016320.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated.

The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Schemes 1A–1C and 2.

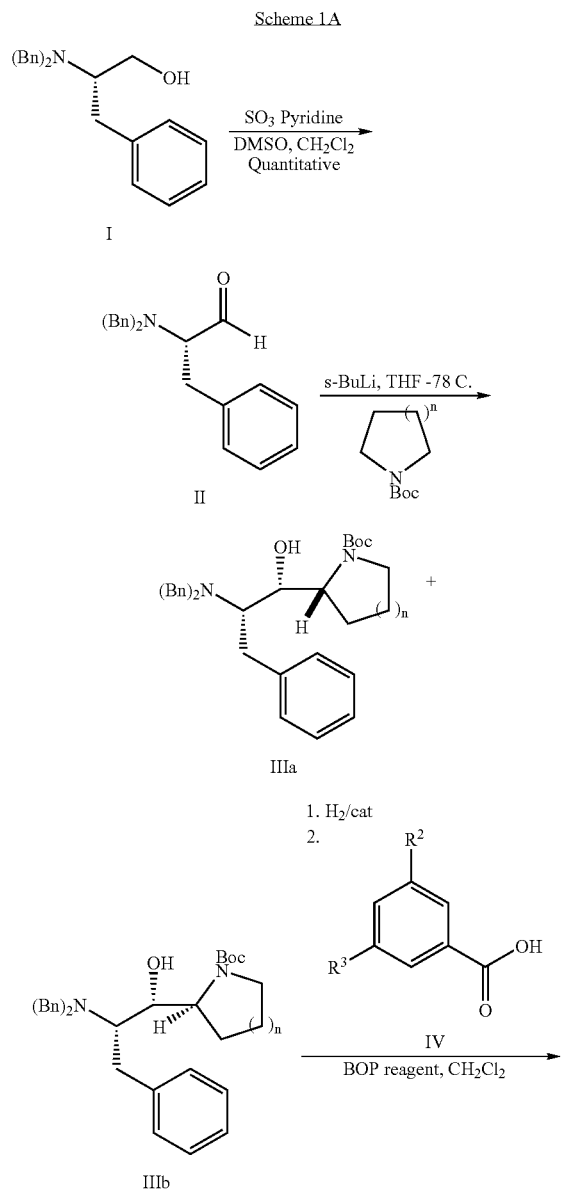

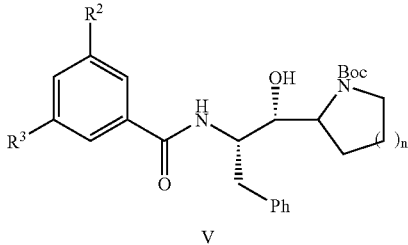

Referring to Scheme 1A, N,N-dibenzyl-L-phenylalanal (II) is obtained by oxidation of the corresponding alcohol (I), and is reacted with an N-Boc-protected cyclic amine in the presence of an alkyl lithium reagent to afford a mixture of protected amine alcohols (III). The N-Boc protected alcohol (III) is debenzylated by catalytic hydrogenation, and coupled to an appropriate benzoic acid (IV) in the presence of BOP reagent and base, to obtain the protected amide V.

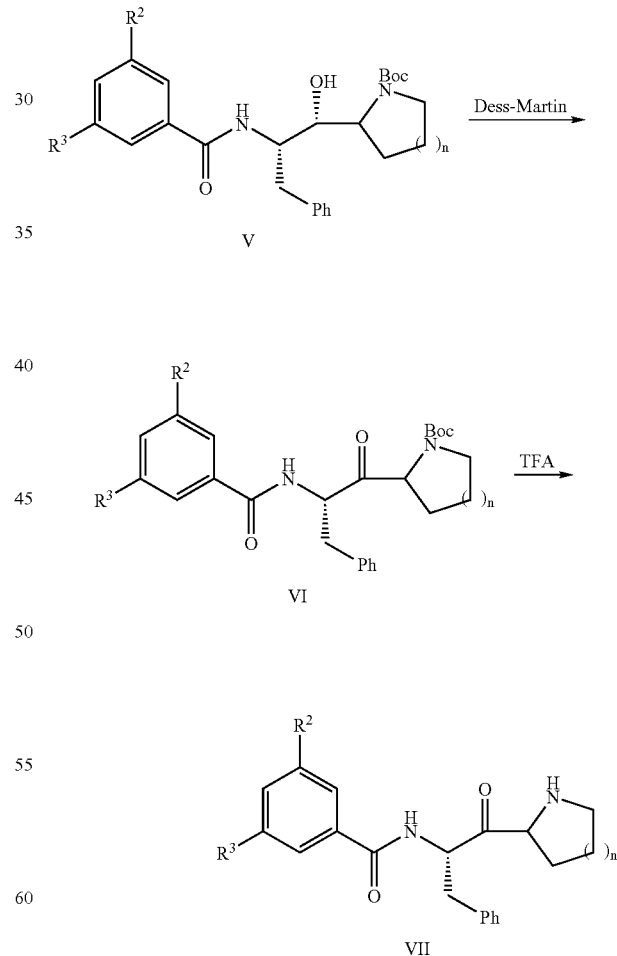

In Scheme IB, the amide (V) is oxidized with the Dess-Martin reagent and deprotected with TFA to provide the final product (VII), to obtain compounds of formula IA.

Scheme 1C

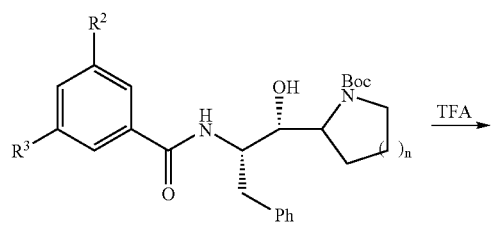

V

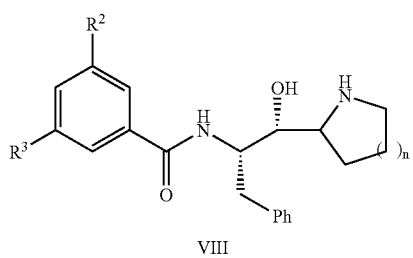

VIII

In Scheme 1C, the amide V is deprotected with TFA to provide the final product VIII, to obtain compounds of formula IB.

A wide variety of N-Boc-protected cyclic amines are applicable to this Scheme, and include examples where the cyclic amine is aziridine, azetidine, pyrrolidine, piperidine, or the like, and also encompasses examples with substitution on other ring carbons, provided that such substitution is inert to the lithiation conditions required in the next step, and allows for a slightly acidic hydrogen adjacent to the nitrogen. Examples of such substitution are alkyl groups, protected alcohols, protected ketones such as ketals or ketone equivalents.

A wide variety of benzoic acids (IV) are applicable to Scheme 1, and include examples where $R^2$ is sulfonamide, sulfone, amide, amine, nitrile, alkylnitrile, halogen, phenyl, and cyanocycloalkyl. $R^3$ of the benzoic acid in Scheme 1 is generally selected from a carboxyaminobenzyl group, a substituted olefin, an O- or N-alkyl cyclopropyl, or an alkyl ether, alkylthioether, or secondary alkylamine.

Scheme 2

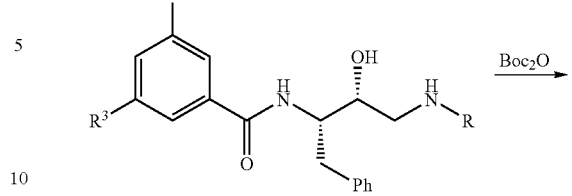

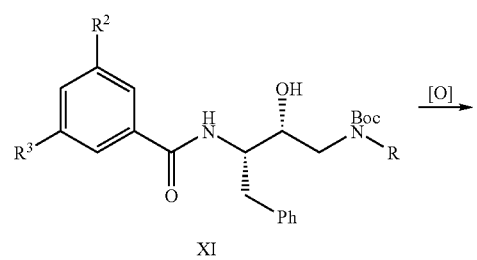

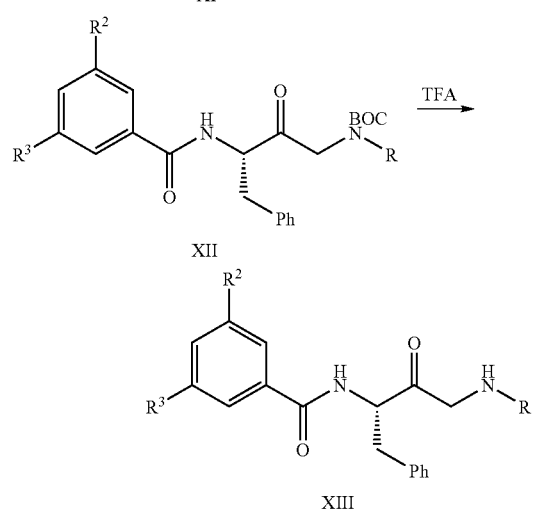

Referring to Scheme 2, an appropriate benzoic acid derivative (IV) is coupled to an appropriate primary amine in the presence of BOP reagent and base to provide an amide (X). This substance is N-protected, oxidized with Dess-Martin reagent, and deprotected to afford the final products (XIII).

A wide variety of benzoic acids are applicable to Scheme 2, and include examples where $R^2$ is sulfonamide, sulfone, amide, amine, nitrile, alkylnitrile, halogen, phenyl, cyanocylcoalkyl. $R^3$ of the benzoic acid in Scheme 2 is generally selected from a carboxyaminobenzyl group, a substituted olefin or an O- or N-alkyl cyclopropyl, or an alkyl ether, alkylthioether, or secondary alkylamine.

In the hydroxyethylamine reactant (IX) of Scheme 2, the R groups are preferably cycloalkanes.

The term "substantially pure" means that the isolated material is at least 90% pure, and preferably 95% pure, and even more preferably 99% pure as assayed by analytical techniques known in the art. The term "substantially enantiomerically pure form" means that at least 90% (preferably 95%, and more preferably 99%) of a compound is present in the form of a single enantiomer. The term "substantially diastereomerically pure form" means that at least 90%

(preferably 95%, and more preferably 99%) of the referenced compound is present in the form of a single diastereomer.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

Utility

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, preventing, ameliorating, controlling or reducing the risk of Alzheimer's disease, other diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment, prevention, control, amelioration, or reduction of risk of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, other beta-secretase inhibitors, gamma-secretase inhibitors, IMG-CoA reductase inhibitors, NSAID's including ibuprofen, N-methyl-D-aspartate (NMDA) receptor antagonists, such as memantine, cholinesterase inhibitors such as galantamine, rivastigmine, donepezil, and tacrine, vitamin E, CB-1 receptor antagonists or CB-1 receptor inverse agonists, antibiotics such as doxycycline and rifampin, anti-amyloid antibodies, or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

Compositions

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, or as soft gelatin capsules wherein the active ingredient is mixed with water or an oil medium.

Aqueous suspensions contain the active materials in admixture with excipients suitable for the manufacture of aqueous suspensions. Such excipients may be suspending agents or dispersing or wetting agents or the like. The aqueous suspensions may also contain one or more preservatives, coloring agents, flavoring agents, or sweetening agents. The compositions for oral use may also be prepared as oily suspensions, or in the form of oil-in-water emulsions, or as syrups or elixirs.

The pharmaceutical compositions may also be in the form of a sterile injectable aqueous or oleagenous suspension, or may be prepared in the form of a suppository for rectal administration of the drug, a topical formulation, an inhalant or as a transdermal patch, according to the knowledge of those skilled in the art or pharmaceutical formulations.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, preventing, controlling, ameliorating, or reducing the risk of Alzheimer's disease or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. The total daily dosage is from about 1.0 milligrams to about 2000 milligrams, preferably from about 0.1 milligrams to about 20 milligrams per kilogram of body weight. In the case of a 70 kg adult human, the total daily dose will generally be from about 7 milligrams to about 1,400 milligrams. This dosage regimen may be adjusted to provide the optimal therapeutic response. The compounds may be administered on a regimen of 1 to 4 times per day, preferably once or twice per day. Exemplary unit dosage forms which may be useful for treatment include 10 mg, 25 mg, 50 mg, 75 mg, 100 mg and 150 mg unit dosage forms.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Biological Activity

The utility of the compounds in accordance with the present invention as inhibitors of β-secretase enzyme activity may be demonstrated by methodology known in the art. Enzyme inhibition is determined as follows.

FRET Assay

A homogeneous end point fluorescence resonance energy transfer (FRET) assay is employed with the substrate ([TAMRA-5-CO-EEISEVNLDAEF-NHQSY]QFRET), which is cleaved by BACE 1 to release the fluorescence from TAMRA. The Km of the substrate is not determined due to the limit of solubility of the substrate. A typical reaction contains approximately 30 nM enzyme, 1.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency of compounds, solutions of inhibitor in DMSO (four concentrations of the inhibitors were prepared: 1 mM, 100 μM, 10 μM, 1 μM) were included in the reactions mixture (final DMSO concentration is 0.8%). All experiments were conducted at room temperature using the standard reaction conditions described above. To determine the IC50 of the compound, competitive equation V0/Vi=1+[I]/[IC50] were employed to predict the inhibitory potency of the compounds. The errors in reproducing the dissociation constants are typically less than two-fold.

HPLC assay

A homogeneous end point HPLC assay is employed with the substrate (coumarin-CO-REVNFEVEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μL. The reaction is proceeded for 30 min and the reaction is stopped by the addition of 25 μL of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at room temperature using the standard reaction conditions described above. To determine the IC50 of the compound, four parameters equation is employed for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 1 μM. Such a result is indicative of the intrinsic activity of the compounds in use as inhibitors of beta-secretase enzyme activity.

Several methods for preparing the compounds of this invention are illustrated in the following Schemes and Examples. Starting materials are made according to procedures known in the art or as illustrated herein. The following examples are provided so that the invention might be more fully understood. These examples are illustrative only and should not be construed as limiting the invention in any way.

Intermediate I

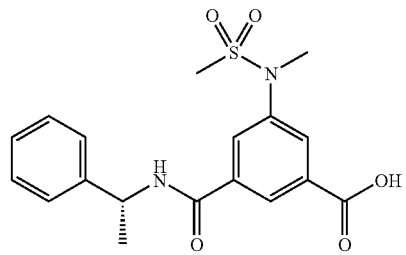

Step A. To a stirred slurry of dimethyl 5-aminoisophthalate (5.0 g, 23.90 mmol) in 100 mL $CH_2Cl_2$/pyridine (3:1) at 0° C. was added methanesulfonyl chloride (1.85 mL, 23.90 mmol). The resulting mixture was stirred for 4 h at room temperature. The solvent was removed in vacuo and ethylacetate (100 mL) was added resulting in precitate formation. The product was collected by filtration to give the sulfonamide as a white solid. $^1$H NMR ($DMSO_{d6}$) δ 8.15 (s, 1H), 8.02 (s, 2H), 3.89 (s, 6H), 3.02 (s, 3H) LCMS $[M-OCH_3]^+$=256.16.

Step B. To a solution of sodium hydride (0.153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with $H_2O$ (100 mL) and extracted with EtOAc (3×50 mL). The organic extracts were dried over $MgSO_4$ and evaporated to give the product. $^1$H NMR ($DMSO_{d6}$) δ 8.40 (s, 1H), 8.19 (s, 2H), 3.91 (s, 6H), 3.34 (s, 3H), 3.01 (s, 3H). LCMS [M+H]=302.15.

Step C. Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to RT over 8 hours. The solution was acidified with 1N HCl (30 mL) and extracted with EtOAc (3×50 mL). The combined organic extracts were washed with brine and dried over $MgSO_4$, filtered and concentrated in vacuo. Purification on silica gel (5% MeOH/$CHCl_3$ containing 1% HOAc) gave the mono acid. $^1$H NMR ($DMSO_{d6}$) δ 8.30 (s, 1H), 8.10 (s, 2H), 3.84 (s, 3H), 3.27 (s, 3H), 2.94 (s, 3H). LCMS (M+H)=288.16.

Step D. A solution containing 0.133 g (0.46 mmol) of the monoacid from step C in 5 mL $CH_2Cl_2$, BOP reagent (0.235 g, 0.55 mmol), (R)-(+)-α-methylbenzylamine (0.071 mL, 0.55 mmol), and diisopropylamine (0.24 mL, 1.39 mmol) was stirred at ambient temperature for 1 h. Evaporation of the solvent and column chromatography on silica gel (90% EtOAc/Hexanes) afforded the benzyl amide. $^1$H NMR ($CDCl_3$) δ 8.26 (s, 1H), 8.17 (s, 1H), 8.06 (s, 1H), 7.31 (m, 5H), 6.50 (d, J=7.1 Hz, 1H), 5.33 (q, J=7.1 Hz, 1H), 3.96 (s, 3H), 3.37 (s, 3H), 2.88 (s, 3H), 1.64 (d, J=7.0 Hz, 3H). LCMS (M+B)=391.20.

Step E. To 0.171 g (0.438 mmol) of the benzyl amide from step D in 10 mL THF:MeOH (1:1) was added 2 N NaOH (0.66 mL, 1.32 mmol). The solution was heated to 50° C. for 1 h. After cooling the solution was acidified by the addition of 1 N HCl (20 mL) and extracted with EtOAc (3×30 mL). The combined organic extractions were dried over $MgSO_4$, filtered, and concentrated in vacuo to yield the desired carboxylic acid. $^1$H NMR ($CDCl_3$) δ 8.22 (t, 1H), 8.11 (m, 1H), 8.06 (m, 1H), 7.34 (m, 5H), 6.47 (d, J=7.1 Hz, 1H), 5.33 (m, 1H), 3.37 (s, 3H), 2.87 (s, 3H), 1.64 (d, J=7.0 Hz, 3H). LCMS (M+H)=377.2.

Intermediate II

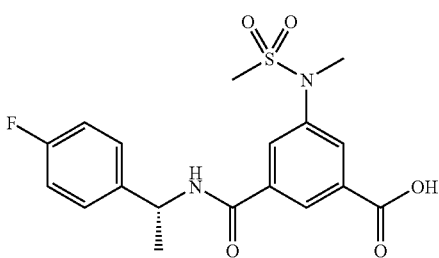

This carboxylic acid was prepared in the same manner as in intermediate I but using (R)-4-fluoro-α-methylbenzyl amine as the amine in step D.

Intermediate III

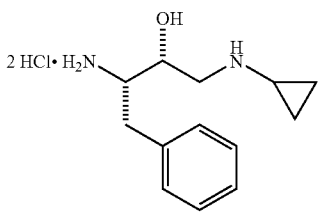

Step A. A solution containing 2.63 g (10.0 mmol) of tert-butyl[S-(R*,R*)]-(–)-(1-oxiranyl-2-phenylethyl)-carbamate in 30 mL of i-PrOH was treated with 6 mL of cyclopropyl amine and heated at 50° C. in a sealed tube for 16 h. The reaction mixture was cooled and evaporated to give the amino alcohol as a white solid that was pure by HPLC and used without further purification. LCMS (M+Na) =239.0.

Step B. A 0° C. solution containing 3.0 g (13.9 mmol) of the Boc protected amino alcohol from step A in 50 mL of 4:1 EtOAc/MeOH was subjected to a slow stream of HCl gas for 15 minutes. After stirring for 3 h, the solvents were removed by rotory evaporation and the resulting solid was triturated with ether and filtered leaving the title compound as a crystalline white solid. LCMS (M+1)=186.3.

Intermediate IV

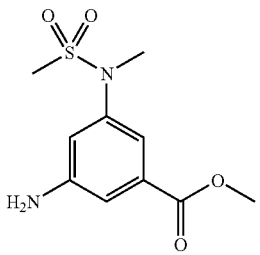

Step A: To 3-amino-5-nitrobenzoic acid (3.60 g, 19.78 mmol) in 100 mL MeOH was added thionyl chloride (2.59 g, 21.76 mmol). The solution was heated to 65° C. for 12 h. Concentration in vacuo afforded the methyl ester hydrochloride salt. $^1$H NMR (CD$_3$OD) δ 8.62 (s, 1H), 8.28 (s, 1H), 8.19 (s, 1H), 3.99 (s, 3H).

Step B: To a solution of 3.53 g (18.0 mmol) amino ester from step A in 100 mL CH$_2$Cl$_2$/pyridine (3:1) was added methanesulfonyl chloride (2.07 g, 18.0 mmol). The reaction was stirred at ambient temperature for 1 h followed by evaporation of the solvent. The gummy residue was taken up in EtOAc (100 mL), acidified with 1N HCl (100 mL), and extracted with EtOAc (3×100 mL). The combined organic extracts were dried over MgSO$_4$, filtered, and concentrated in vacuo to provide the sulfonamide as an off-white solid. $^1$H NMR (CD$_3$OD) δ 8.46 (s, 1H), 8.30 (s, 1H), 8.18 (s, 1H), 3.97 (s, 3H), 3.09 (s, 3H).

Step C: Sodium Hydride (0.26 g, 6.55 mmol, 60% oil dispersion) was suspended in 10 mL DMF to which 1.5 g (5.45 mmol) of the sulfonamide from step B (in 10 mL DMF) was added followed by 0.93 g (6.55 mL) methyl iodide. The solution was stirred at ambient temperature for 3 h. The reaction was quenched with H$_2$O (250 mL), extracted with EtOAc (3×200 mL), dried over MgSO$_4$, filtered and concentrated in vacuo. Purification by silica gel chromatography provided the N-methyl sulfonamide. LCMS (M–H$_2$O)=272.2.

Step D. To a solution of the nitro sulfonamide (2.7 g, mmol) from step C and 0.15 g of 10% Pd/C in 50 mL EtOH containing HOAc (2 mL) was stirred at room temperature under a balloon of hydrogen gas for 12 h. The mixture was filtered through a pad of Celite, concentrated, and purified on silica gel (100% EtOAc) to afford the desired aniline. $^1$H NMR (CD$_3$OD) δ 7.29 (s, 1H), 7.26 (s, 1H), 6.95 (s, 1H), 3.87 (s, 3H), 3.27 (sm 3H), 2.89 (s, 3H). LCMS (M+H) =258.2.

Intermediate V

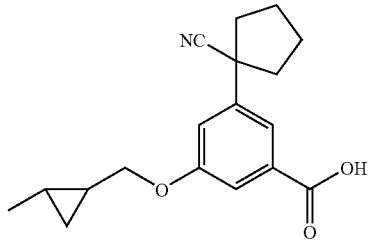

Step A. To a stirred solution of dimethyl 5-hydroxyisophthalate (8.6 g, 41.1 mmol) in 200 mL of acetone was added K$_2$CO$_3$ (5.7 g, 41.1 mmol) and trans-crotyl bromide (5.5 g, 41.1 mmol). The resulting mixture was stirred at reflux for 16 h. The solids were removed by filtration and the filtrate was evaporated to near dryness. The resulting residue was dissolved in 200 mL of ether and washed 3×20 mL of 1N HCl then brine. The organic extracts were dried over MgSO$_4$ and evaporated to give aryl ether A. $^1$H NMR (CDCl$_3$) δ 8.25 (s, 1H), 7.75 (s, 2H), 5.93 (m, 1H), 5.77 (m, 1H), 4.58 (d, J=2.2 Hz, 2H), 3.91 (s, 6H), 1.81 (d, J=2.2 Hz, 3H). LCMS (M+H)=265.24.

Step B. A 0° C. solution containing 9.4 g (35.6 mmol) of the isophthalate from step A in 300 mL of a 1:1 mixture of THF and MeOH was treated with 35.6 mL (35.6 mmol) of 1N NaOH. The ice bath was allowed to stir to ambient temperature over 16 h. The reaction mixture was concentrated to ca. ⅛ volume before it was acidified with 25 mL of 3N HCl. The solids that precipitated were redissolved in 300 mL of EtOAc and washed with brine (2×25 mL). The organic extract was dried over MgSO₄ and evaporated to afford the desired carboxylic acid. ¹H NMR (CDCl₃) δ 8.37 (s, 1H), 7.82 (s, 2H), 5.93 (m, 1H), 5.77 (m, 1H), 4.58 (d, J=2.2 Hz, 2H), 3.95 (s, 3H), 1.77 (d, J=2.2 Hz, 3H). LCMS (M+H)=252.18

Step C. To a solution containing 2.5 g (10.0 mmol) of carboxylic acid from step B in 100 mL of THF was added 1.78 g (11.0 mmol) of CDI. The resulting solution was stirred for 1 h then treated with 741 mg (20.0 mmol) of NaBH₄ dissolved in 5 mL of water. After an additional hour at rt the reaction mixture was diluted with 200 mL of ether and quenched with 25 mL of 1N HCl. The organic phase was separated and dried over MgSO₄. Column chromatograhy (1:1 EtOAc/Hexanes) afforded of benzylic alcohol C. ¹H NMR (CDCl₃) δ 7.68 (s, 1H), 7.44 (s, 1H), 7.11 (s, 1H), 5.85 (m, 1H), 5.65 (m, 1H), 5.20 (s, 2H), 4.74 (d, J=6.0 Hz, 2H), 4.444 (s, 2H), 3.82 (s, 3H), 1.71 (d, 3H). LCMS (M+H)= 237.22

Step D. A 0° C. solution of 1.65 g (7.0 mmol) of the alcohol from step C was dissolved in 50 mL of DCM and treated with 2.0 g (7.7 mmol) of triphenylphosphine then 2.6 g (7.7 mmol) of CBr₄. The reaction mixture was stirred to rt over 16 h, concentrated and chromatographed (1:4 EtOAc/Hexanes) to afford the benzylic bromide D. ¹H NMR (CDCl₃) 7.62 (s, 1H), 7.44 (s, 1H), 7.11 (s, 1H), 5.85 (m, 1H), 5.65 (m, 1H), 4.50 (d, J=6.0 Hz, 2H), 4.46 (s, 2H), 3.90 (s, 3H), 1.71 (d, 3H). LCMS (M+H)=299.13

Step E. To a solution of the benzylic bromide (2.1 g, 7.0 mmol) from step D in 50 mL of MeCN was added 1.05 g of TMSCN then 1 M TBAF in THF (10.5 mL). The reaction mixture was stirred at room temperature for 15 h after which the solvent was removed and the residue chromatographed over silica gel (3:7 EtOAc/Hexanes) to afford the desired nitrile. ¹H NMR (CDCl₃) 7.62 (s, 1H), 7.58 (s, 1H), 7.07 (s, 1H), 5.85 (m, 1H), 5.65 (m, 1H), 4.50 (d, J=6.0 Hz, 2H), 3.97 (s, 3H), 3.75 (s, 3H), 1.79 (d, 3H). LCMS (M−13)= 233.1.

Step F. To a 0° C. solution of the compound from step E (1.27 g, 5.2 mmol) in 0.5 mL of THF was added 1.2 g (5.2 mmol) of benzyl triethylammonium chloride, 1.3 mL (11.0 mmol) of 1,3-dibromopropane and 10.0 mL (100.0 mmol) of 10.0 N NaOH. The ice bath was removed after 5 min and the reaction mixture was stirred to rt over 20 h. The reaction was acidified with 12 N HCl (10 mL) and extracted with EtOAc (3×50 mL). The organic phase was dried and concentrated to afford the crude cyclopentylnitrile. This material was redissolved in 15 mL of EtOAc and treated with 45 mL of 0.5 M ethereal CH₂N₂. After 5 minutes, 64 mg (0.2 mmol) of Pd(OAc)₂ was added to effect effervescence. The reaction was stirred 1 h, filtered through Celite, concentrated and chromatographed (1:3 EtOAc/Hexane) to give the desired compound. ¹H NMR (CDCl₃) δ 7.62 (s, 1H), 7.47 (s, 1H), 7.12 (s, 1H), 3.87 (s, 3H), 3.83 (m, 2H), 2.44 (m, 2H), 2.15–1.94 (m, 6H), 1.79 (d, 3H) 0.97 (m, 2H0, 0.75 (m, 2H), 0.55 (m, 2H), 0.41 (m, 2H).

Step H. To a stirred solution of the ester from step F (801 mg, 2.56 mmol) in 20 mL THF/MeOH (1:1) was added 15% NaOH (2.2 mL, 8.0 mmol). After the reaction mixture was stirred at 45° C. for 2 h the solvents were evaporated and the residue was acidified with 3N HCl (4.0 mL, 12 mmol). The solid was taken up in 75 mL of DCM and the organic phase was washed with brine. The organic phase was dried and evaporated to yield the desired carboxylic acid as a white solid that was used without further purification.

Intermediate VI

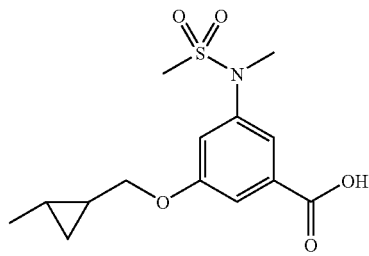

Step A. To a stirred solution of dimethyl 5-hydroxyisophthalate (8.6 g, 41.1 mmol) in 200 mL of acetone was added K₂CO₃ (5.7 g, 41.1 mmol) and trans-crotyl bromide (5.5 g, 41.1 mmol). The resulting mixture was stirred at reflux for 16 h. The solids were removed by filtration and the filtrate was evaporated to near dryness. The resulting residue was dissolved in 200 mL of ether and washed 3×20 mL of 1N HCl then brine. The organic extracts were dried over MgSO₄ and evaporated to give aryl ether VI-A. ¹H NMR (CDCl₃) δ 8.25 (s, 1H), 7.75 (s, 2H), 5.93 (m, 1H), 5.77 (m, 1H), 4.58 (d, J=2.2 Hz, 2H), 3.91 (s, 6H), 1.81 (d, J=2.2 Hz, 3H). LCMS (M+H)=265.24.

Step B. A 0° C. solution containing 9.4 g (35.6 mmol) of the isophthalate from step A in 300 mL of a 1:1 mixture of THF and MeOH was treated with 35.6 mL (35.6 mmol) of 1N NaOH. The ice bath was allowed to stir to ambient temperature over 16 h. The reaction mixture was concentrated to ca. ⅛ volume before it was acidified with 25 mL of 3N HCl. The solids that precipitated were redissolved in 300 mL of EtOAc and washed with brine (2×25 mL). The organic extract was dried over MgSO₄ and evaporated to afford the desired carboxylic acid. ¹H NMR (CDCl₃) δ 8.37 (s, 1H), 7.82 (s, 2H), 5.93 (m, 1H), 5.77 (m, 1H), 4.58 (d, J=2.2 Hz, 2H), 3.95 (s, 3H), 1.77 (d, J=2.2 Hz, 3H). LCMS (M+H)=252.18

Step C. To a 0° C. solution containing 4.0 g (16.0 mmol) of carboxylic acid VI-C in 80 mL of THF was added 4.2 mL (30.2 mmol) of Et₃N and 2.2 mL (22.7 mmol) of ethyl chloroformate. The resulting slurry was stirred for 1 h and treated with 2.46 g (37.8 mmol) of NaN₃ dissolved in 15 mL of water. After an additional hour at rt the reaction mixture was diluted with 50 mL of water and washed toluene (3×50 mL). The combined organic extracts were dried over MgSO₄ and refluxed over 16 h. The reaction was cooled to rt and treated with 3.1 mL (30.2 mmol) of benzyl alcohol and 4.2 mL (30.2 mL) of triethylamine. The reaction was refluxed for 24 h, cooled and diluted with 100 mL of EtOAc and 35 mL of 10% citric acid. The organic extract was washed with water and brine then dried over MgSO₄. Column chromatograhy (2:3 EtOAc/Hexanes) afforded the carbamate VI-C. ¹H NMR (CDCl₃) δ 7.38 (m, 8H), 6.85 (bs, 1H), 5.85 (m, 1H), 5.65 (m, 1H), 5.20 (s, 21), 4.44 (d, J=6.0 Hz, 2H), 3.82 (s, 3H), 1.71 (d, 3H). LCMS (M+H)=356.25

Step D. A solution of 3.56 g (10.0 mmol) of the aryl ether from step C was dissolved in 100 mL of EtOAc and treated with 50 mL (c.a. 0.5 M, 25 mmol) of freshly prepared CH₂N₂. After stirring for 5 minutes, 112 mg (0.5 mmol) of Pd(OAc)₂ was added to effect vigorous release of N₂. After an additional 30 minutes, the brown slurry was evaporated and chromatographed (1:1 EtOAc/Hexanes) to the cyclopropylmethyl ether VI-D. ¹H NMR (CDCl₃) δ 7.55 (s, 1H), 7.44 (m, 7H), 6.80 (bs, 1H), 5.23 (s, 2H), 3.85 (s, 3H), 3.80

(m, 2H), 1.04 (d, 3H), 0.94 (m, 1H), 0.75 (m, 1H), 0.47 (m, 1H), 0.38 (m, 1H). LCMS (M+H)=368.26

Step E. To a solution of the benzyl carbamate (3.6 g, 10.0 mmol) from step D and 1.5 g of 10% Pd/C in EtOAc (100 mL) was stirred at room temperature under a balloon of hydrogen gas for 5 h. The mixture was filtered through a pad of Celite, concentrated, and purified on silica gel (50% EtOAc/Hexanes) to afford the desired aniline. $^1$H NMR (CDCl$_3$) δ 6.99 (s, 2H), 6.40 (s, 1H), 3.85 (s, 3H), 3.75 (m, 2H), 1.77 (m, 1H), 1.45 (m, 1H), 1.04 (d, 3H), 0.47 (m, 1H), 0.33 (m, 1H). LCMS (M+H)=236.2.

Step F. To a 0° C. solution of the aniline from step E (940 mg, 4.0 mmol) in 30 mL of CH$_2$Cl$_2$ and 5 mL of pyridine was added methanesulfonyl chloride (0.40 mL, 4.0 mmol). The resulting mixture was stirred at this temperature for 2 h before being diluted with 100 mL of DCM. The solution was washed with 1N HCl (3×25 mL), water (2×25 mL), and brine (25 mL). The organic phase was dried and concentrated to afford sulfonamide VI-F that was used in the next step without further purification. LCMS (M+H)=314.1

Step G. The sulfonamide from step F (1.25 g, 4:0 mmol) in DMF (20 mL) was treated with 95% sodium hydride (106 mg, 4.4 mmol) and excess methyl iodide (3 mL). The resulting mixture was stirred at ambient temperature for 1 h and was diluted with 200 mL of ether. The solution was washed with water (7×25 mL) and brine then dried over MgSO$_4$. Purification by silica gel chromatography (2:3 EtOAc/Hexanes) afforded of the desired methylated sulfonamide. $^1$H NMR (CDCl$_3$ w/0.05% DMSO-d$_6$) δ 7.65 (s, 1H), 7.41 (s, 1H), 7.15 (s, 1H), 3.93 (s, 3H), 3.80 (t, 2H), 3.30 (s, 3H), 2.87 (s, 3H), 1.11 (d, 3H), 0.88 (m, 1H), 0.55 (m, 1H), 0.37 (m, 1H). LCMS (M+1)=328.23

Step H. To a stirred solution of the ester from step G (625 mg, 2.0 mmol) in 12 mL THF/MeOH (1:1) was added 15% NaOH (2.2 mL, 8.0 mmol). After the reaction mixture was stirred at 45° C. for 2 h the solvents were evaporated and the residue was acidified with 3N HCl (4.0 mL, 12 mmol). The solid was taken up in 75 mL of DCM and the organic phase was washed with brine. The organic phase was dried and evaporated to yield of the desired carboxylic acid as a white solid. $^1$H NMR (CDCl$_3$ w/0.05% DMSO-d6) δ 7.61 (s, 1H), 7.44 (s, 1H), 7.15 (s, 1H), 3.83 (t, 2H), 3.32 (S, 3H), 2.83 (s, 3H), 1.11 (d, 3H), 0.88 (m, 1H), 0.55 (m, 1H), 0.37 (m, 1H). LCMS (M+H)=314.22

EXAMPLE 1

R, S, R Diastereomer

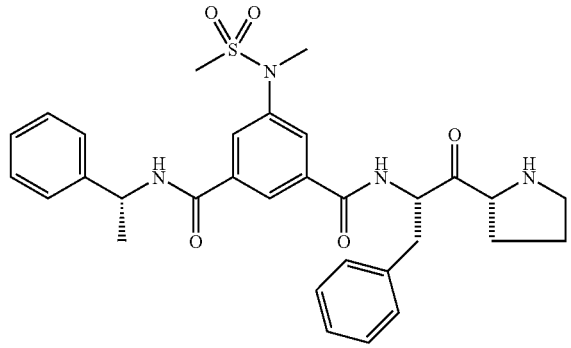

Step A. To a −70° C. solution containing 2.57 g (15.01 mmol) of N-Boc-pyrrolidine in 75 mL of ether was added 1.4 M sec-BuLi (11.8 ml, 16.5 mmol). The resulting reaction mixture was stirred at this temperature for 4 h then treated with 4.94 g (15.01 mmol) of N,N-dibenzyl-L-phenylalanal in 20 mL of ether. The reaction was complete within 5 minutes. The reaction mixture was quenched with 50 mL of saturated NaHCO$_3$ and extracted with EtOAc (3×50 mL). The combined organic extracts were washed with water and brine (2×25 mL). Evaporation of the solvent and column chromatography (1:4 EtOAc/Hexanes) afforded the (S, R, R) diastereomer and the (S, R, S) diasteromer. (S, R, R) Diastereomer: $^1$H NMR (CDCl$_3$) δ 7.34–7.10 (m, 15H), 4.19 (m, 1H), 3.82–2.90 (m, 9H), 1.83 (m, 2H), 1.47 (s, 9H), 1.26 (m, 4H). LCMS (M+H)=501.3. (S, R, S) Diastereomer: $^1$H NMR (CDCl$_3$) δ 7.29 (m, 15H), 4.96 (m, 1H), 3.96 (d, J=14.5 Hz, 2H), 3.78 (m 1H), 3.56 (d, J=14.5 Hz, 2H), 3.33 (m, 3H), 3.07 (m, 1H), 2.84 (m, 2H), 1.83 (m, 4H), 1.47 (s, 9H). LCMS (M+H)=501.3.

Step B. A solution containing 0.130 g (0.259 mmol) of the (S, R, R) dibenzylamine from step A and a catalytic amount of 10% Pd(OH)$_2$ in 5 mL of MeOH was hydrogenated under a balloon of hydrogen gas for 16 h. The mixture was filtered through a pad of Celite and evaporated to give the desired amine as an oil. LCMS (M+H)=321.3.

Step C. A solution containing 92 mg (0.24 mmol) of the intermediate acid I in 5 mL of CH$_2$Cl$_2$ was treated sequentially with BOP reagent (103 mg, 0.24 mmol), the (S, R, R) amine from step B (78 mg, 0.24 mmol), and diisopropylethylamine (0.13 mL, 0.72 mmol). The reaction mixture was stirred at ambient temperature for 30 minutes. Evaporation of the solvent and purification reverse phase HPLC afforded the amide. LCMS (M+H)=679.3.

Step D. To 50 mg (0.074 mmol) of the Boc-protected amine from step C dissolved in 3 mL CH$_2$Cl$_2$ was added Dess-Martin periodinane (0.094 g, 0.222 mmol) and the solution was stirred at ambient temperature for 1 h. The solvent was evaporated and the crude solution was treated with 2.5 mL CH$_2$Cl$_2$:TFA (4:1) and stirred 15 min at ambient temperature. The reaction was evaporated and purified by reverse phase HPLC to afford the desired compound as its TFA salt. $^1$H NMR (CD$_3$OD) δ 8.88 (d, J=7.7 Hz, 1H), 8.12 (s, 1H), 8.03 (s, 1H), 7.90 (s, 1H), 7.41–7.21 (m, 10H), 5.24 (t, J=7.1 Hz, 1H), 4.71 (t, J=8.1 Hz, 1H), 3.35 (s, 3H), 3.40–3.30 (m, 1H), 3.11 (dd, J=14, 9.4 Hz, 1H), 2.96 (s, 3H), 2.28 (m, 1H), 2.02–1.92 (m, 2H), 1.82 (m, 2H), 1.58 (d, J=6.9 Hz, 3H). LCMS (M+H)=577.3.

EXAMPLE 2

R, S, S Diastereomer

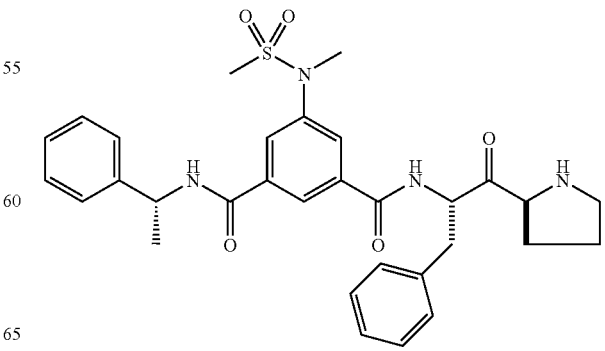

Step A. A solution containing 146 mg (0.39 mmol) of the intermediate acid I in 5 mL of CH$_2$Cl$_2$ was treated sequentially with BOP reagent (164 mg, 0.39 mmol), the (S, R, S) amine from Example 1, step B (150 mg, 0.48 mmol), and diisopropylethylamine (0.21 mL, 1.17 mmol). The reaction mixture was stirred at ambient temperature for 30 minutes. Evaporation of the solvent and purification reverse phase HPLC to afford the amide. LCMS (M+H)=679.3.

Step B. To 50 mg (0.074 mmol) of the Boc-protected amine from step A dissolved in 3 mL of CH$_2$Cl$_2$ was added Dess-Martin periodinane (0.094 g, 0.222 mmol) and the solution was stirred at ambient temperature for 1 h. The solvent was evaporated and the crude solution was treated with 2.5 mL CH$_2$Cl$_2$:TFA (4:1) and stirred 15 min at ambient temperature. The reaction was evaporated and purified by reverse phase HPLC to afford the desired compound as its TFA salt. $^1$H NMR (CD$_3$OD) δ 8.89 (d, J=7.7 Hz, 1H), 8.12 (s, 1H), 8.02 (s, 1H), 7.91 (s, 1H), 7.41–7.24 (m, 10H), 5.24 (m 1H), 5.07 (dd, J=9.4, 6.1 Hz, 1H), 4.37 (t, J=7.0, 1H), 3.48 (q, J=7.1 HZ, 1H), 3.35 (s, 3H), 3.10 (dd, J=14, 7.1 Hz, 1H), 2.95 (s, 3H), 2.43 (m, 2H), 2.04 (m, 2H), 1.57 (d, J=7.1 Hz, 3H). LCMS (M+H)=577.2.

EXAMPLE 3

R, S, R Diastereomer

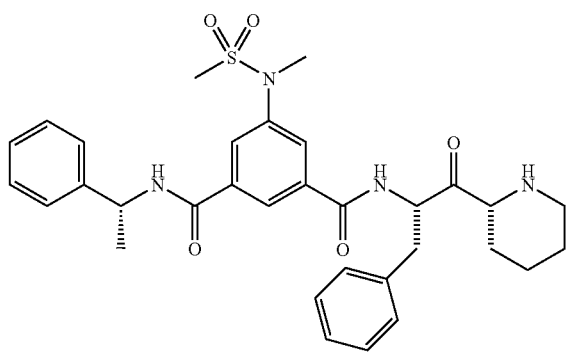

Step A. To a −70° C. solution containing 1.12 g (6.05 mmol) of N-Boc-piperidine in 15 mL of ether was added TMEDA (0.77 g, 6.66 mmol) then 1.4 M sec-BuLi (4.76 ml, 6.66 mmol). The resulting reaction mixture was stirred at this temperature for 1 h then, warmed to −20° C. for 10 min, recooled to −70° C. then treated with 2.0 g (6.05 mmol) of N,N-dibenzyl-L-phenylalanal in 5 mL of ether. The reaction was complete within 10 minutes but was allowed to stir to rt over 4 h to effect cyclization of the undesired erythro isomer (e.g see Beak and Lee, J. Org. Chem. 1993, 58, 1109–1117). The reaction mixture was quenched with 50 mL of saturated NaHCO$_3$ and extracted with EtOAc (3×50 mL). The combined organic extracts were washed with water and brine (2×25 mL). Evaporation of the solvent and column chromatography (1:4 EtOAc/Hexanes) afforded the diastereomerically pure alcohol. $^1$H NMR (CDCl$_3$) δ 7.30 (m, 15H), 4.40 (m, 1H), 4.15 (m, 1H), 3.83 (d, J=14 Hz, 2H), 3.73 (m, 1H), 3.59 (d, J=14 Hz, 2H), 3.10–2.91 (m, 3H), 2.74 (m, 1H), 1.94 (m 1H), 1.67–0.94 (m, 6H), 1.39 (s, 9H). LCMS (M+H)=515.4.

Step B. A solution containing 0.158 g (0.307 mmol) of the dibenzylamine from step A and a catalytic amount of 10% Pd(OH)$_2$ in 10 mL of MeOH was hydrogenated under a balloon of hydrogen gas for 48 h. The mixture was filtered through a pad of Celite and evaporated to give the desired amine as an oil. LCMS (M+H)=335.3.

Step C. A solution containing 90 mg (0.24 mmol) of the intermediate acid I in 5 mL of CH$_2$Cl$_2$ was treated sequentially with BOP reagent (101 mg, 0.24 mmol), the amine from step B (80 mg, 0.24 mmol), and diisopropylethylamine (0.13 mL, 0.72 mmol). The reaction mixture was stirred at ambient temperature for 30 minutes. Evaporation of the solvent and purification by silica gel chromatography (100% EtOAc) afforded the amide. $^1$H NMR (CDCl$_3$) δ 7.93–7.10 (m, 14 H), 6.77 (d, J=7.4 Hz, 1H), 5.26 (m, 1H), 4.41 (m, 1H), 4.32 (m, 1H), 4.07 (m, 1H), 3.28 (s, 3H), 3.08 (m, 1H), 2.89 (s, 3H), 2.95–2.71 (m, 2H), 2.15 (m 1H), 1.73–1.43 (m, 7H), 1.59 (d, J=7.0 Hz, 3 H), 1.51. (s, 9H). LCMS (M−BOC)= 593.3.

Step D. To 65 mg (0.094 mmol) of the Boc-protected amine from step C was dissolved in 3 mL of CH$_2$Cl$_2$ was added Dess-Martin periodinane (0.12 g, 0.28 mmol) and the solution was stirred at ambient temperature for 2 h. The solvent was evaporated and the crude solution was treated with 2.5 mL CH$_2$Cl$_2$:TFA (4:1) and stirred 15 min at ambient temperature. The reaction was evaporated and purified by reverse phase HPLC to afford of the desired compound as its TFA salt. $^1$H NMR (CD$_3$OD) δ 8.88 (d, J=7.42 Hz, 1H), 8.13 (s, 1H), 8.04 (s, 1H), 7.92 (s, 1H), 7.42–7.20 (m, 10H), 5.27 (m, 1H), 4.26 (dd, J=12, 3.0 Hz, 1H), 3.48–3.28 (m, 2H), 3.36 (s, 3H), 3.10 (dd, J=13, 9.0 Hz, 1H), 2.97 (s, 3H), 2.22 (m, 1H), 1.85 (m, 2H), 1.60 (d, J=7.0 Hz, 3H), 1.62–1.58 (m, 1H), 1.36–1.30 (m, 2H). LCMS (M+H)=591.3.

EXAMPLE 4

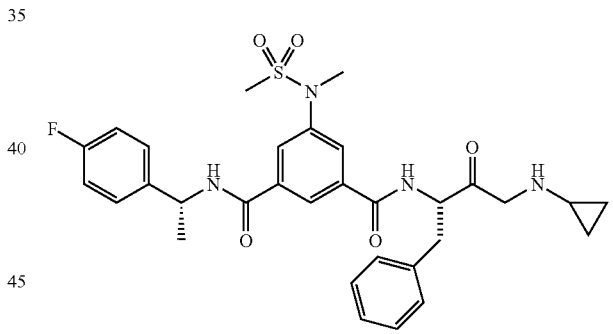

Step A. A solution containing 20.0 mg (0.054 mmol) of intermediate II in 2 mL of CHCl$_3$ was treated sequentially with BOP reagent (24.0 mg, 0.054 mmol), the amine intermediate III (19.0 mg, 0.064 mmol), and diisopropylethylamine (0.021 mL, 0.12 mmol). The reaction mixture was stirred at ambient temperature for ten minutes. Evaporation of the solvent and purification by reverse phase HPLC afforded the amino alcohol. $^1$H NMR (CD$_3$OD) δ 8.87 (d, 1H), 8.32 (s, 1H), 7.98 (d, 2H), 7.78 (s, 1H), 7.36 (m, 4H), 7.25 (m, 5H), 5.23 (m, 1H), 4.24 (m, 1H), 3.96 (m, 1H), 3.33 (s, 3H), 3.19 (m, 2H), 2.94 (s, 3H), 2.80 (m, 3H), 1.57 (d, 3H), 0.89 (m, 4H). LCMS (M+H)=597.3.

Step B. To the amino alcohol (0.204 g, 0.342 mmol) from step A in 5 mL acetonitrile was added di-tert-butyldicarbonate (0.097 g, 0.45 mmol) followed by diisopropylethylamine (0.13 g, 1.03 mmol). The reaction was stirred at ambient temperature for 16 hours, concentrated in vacuo and purified by silica gel chromatography (80% EtOAc/Hexanes) to afford the Boc-protected amine. LCMS (M+H)=697.1.

Step C. To 47 mg (0.067 mmol) of the Boc-protected amine from step B dissolved in 3 mL CH$_2$Cl$_2$ was added Dess-Martin periodinane (0.086 g, 0.202 mmol) and the solution was stirred at ambient temperature for 2 h. The solvent was evaporated and the crude solution treated with 2.5 mL CH$_2$Cl$_2$:TFA (4:1) and stirred 30 min at ambient temperature. The reaction was evaporated and purified by reverse phase HPLC to afford the desired compound as its TFA salt. $^1$H NMR (CD$_3$OD) δ 8.89 (d, J=7.9 Hz, 1H), 8.13 (s, 1H), 8.02 (s, 1H), 7.93 (s, 1H), 7.42 (dd, J=8.2, 5.4 Hz, 2H), 7.34–7.24 (m, 5H), 7.06 (t, J=8.7 Hz, 2H), 5.24 (m, 1H), 4.81 (m, 1H), 4.39 (d, J=18 Hz, 1H), 3.97 (d, J=18 Hz, 1H), 3.36 (s, 3H), 3.14 (dd, J=14, 9.1 Hz, 1H), 2.96 (s, 3H), 2.70 (m, 1H), 1.57 (d, J=7.1 Hz, 3H), 0.96–0.83 (m 5H). LCMS (M+H)=595.3.

EXAMPLE 5

R, S, R, S Diastereomer

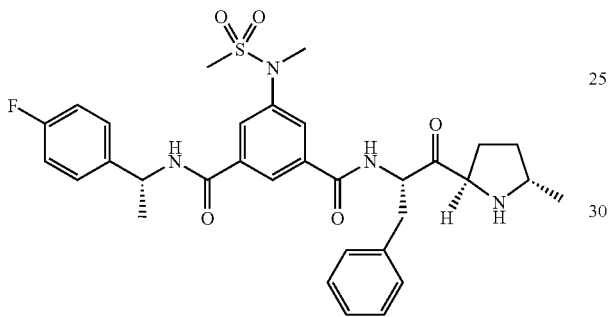

Step A. To a stirred mixture of 1.1 g (6.1 mmol) of (S)-N-Boc-2-methylpyrrolidine (preparation: Donner, B. G. *Tetrahedron Letters* 1995, 36, 1223–1226) and 0.70 g (6.08 mmol) N,N,N',N'-tetramethylethylenediamine in 12 mL of ether at −78° C., 5.2 mL of 1.4M sec-butyllithium was added dropwise. The reaction mixture was stirred at −78° C. for 40 min. A solution of the N,N-dibenzyl-L-phenylalanal in 6 mL ether was then added to the reaction mixture. The reaction was warmed to room temperature over 16 h. The reaction was quenched with 100 mL of saturated bicarb and the mixture was extracted with EtOAc (3×50 mL). The combined organics were washed with brine (100 mL) before being dried over MgSO$_4$, filtered, and concentrated in vacuo. The residue was purified by silica gel chromatography (5%–60% EtOAc:Hexanes). The isolated product was then purified by reverse phase HPLC. Lyophilization provided the dibenzylamine. $^1$H NMR (CD$_3$OD) δ 8.87 (s, 1H), 8.10 (s, 1H), 7.91 (s, 1H), 7.77 (d, J=7.7 Hz, 1H), 7.65–7.14 (m, 13 H), 5.24 (m, 1H), 4.21 (m, 1H), 3.97 (m, 1H), 3.21 (m, 1H), 2.78 (m, 2H), 2.28 (m, 1H), 2.26 (s, 3H), 1.56 (d, J=7.1 Hz, 3H), 0.91 (m, 4H). LCMS (M+H)=515.4.

Step B. A solution containing 0.031 g (0.060 mmol) of from step A in 1 mL MeOH was treated with a catalytic amount of Pearlman's catalyst and stirred at room temperature under a hydrogen atmosphere for 40 min. The reaction was filtered through plug of celite and the solvent was removed in vacuo to afford the corresponding amine. LCMS (M+H)=335.4.

Step C: A solution containing 22 mg (0.055 mmol) of the intermediate acid II in 3 mL of CH$_2$Cl$_2$ was treated sequentially with BOP reagent (24 mg, 0.055 mmol), the (S, R, R) amine from step B (20 mg, 0.055 mmol), and diisopropylethylamine (0.03 mL, 0.167 mmol). The reaction mixture was stirred at ambient temperature for 30 minutes. Evaporation of the solvent and purification reverse phase HPLC to afford the amide. LCMS (M+H)=711.3.

Step D. A solution containing 0.0092 g (0.013 mmol) of amide from step C in 1 mL CH$_2$Cl$_2$ at 0° C. was treated with 0.011 g (0.026 mmol) of Dess-Martin periodinane. The reaction mixture was warmed to room temperature and stirred for 1 h. The solvent was removed in vacuo and the residue was purified by reverse phase HPLC. Lyophilization provided the ketone. LCMS (M-Boc)=609.3.

Step E. A solution containing 0.0081 g (0.011 mmol) of the ketone from step D in 1 mL CH$_2$Cl$_2$ at 0° C. was treated with 1 mL TFA. The reaction was stirred at 0° C. for 10 min. The solvents were removed in vacuo to afford the desired amino ketone. LCMS (M+H)=609.6. $^1$H NMR (CD$_3$OD) δ 8.90 (d, J=7.7 Hz, 1 H), 8.11 (m, 1H), 8.03 (m, 1H), 7.90 (m, 1H), 7.42 (m, 2H), 7.30–7.19 (m, 4H), 7.06 (t, 2H), 5.23 (m, 1H), 4.76 (m, 1H), 3.66 (m, 1H), 3.35 (s, 3H), 3.11 (m, 1H), 2.96 (s, 3H), 2.39 (m, 1H), 2.15 (m, 1H), 1.81 (m, 2H), 1.72–1.62 (m, 2H), 1.57 (d, J=7.0 Hz, 3H), 1.40 (d, J=6.6 Hz, 3H).

EXAMPLE 6

Trans (RR,SS), S

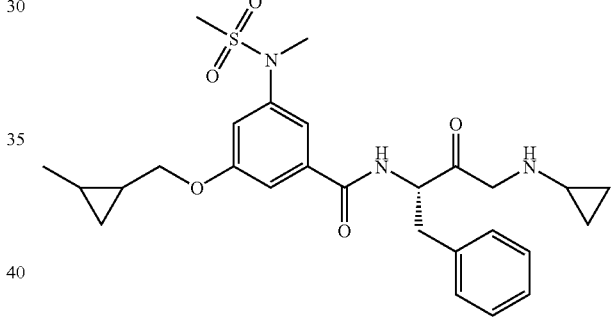

Step A: A solution containing 0.25 g (0.80 mmol) of the intermediate acid VI in 10 mL of CH$_2$Cl$_2$ was treated sequentially with BOP reagent (0.338 g, 0.80 mmol), the amine from intermediate III (0.234 mg, 0.80 mmol), and diisopropylethylamine (0.31 g, 2.40 mmol). The reaction mixture was stirred at ambient temperature for 30 minutes. Evaporation of the solvent and purification with reverse phase HPLC afforded the amide. LCMS (M+H)=516.3.

Step B. A solution containing 0.31 g (0.61 mmol) of amide from step A, 0.16 g (0.73 mmol) of di-tert-butyl dicarbonate: and 0.094 g (0.73 mmol) of DIPEA was stirred in 6 mL of ACN at 50° C. for 1.5 h. The reaction mixture was cooled and the solvent was removed in vacuo to afford the Boc amine. LCMS (M-Boc)=616.4.

Step C. A solution containing 0.33 g (0.53 mmol) of the Boc amine from step B in 5 mL CH$_2$Cl$_2$ at 0° C. was treated with 0.45 g (0.11 mmol) of Dess-Martin periodinane. The reaction mixture was warmed to room temperature and stirred for 30 min. The solvent was removed in vacuo and the residue was purified by reverse phase HPLC. Lyophilization provided the Boc amino ketone. LCMS (M-Boc)= 514.3.

Step D. A solution containing 0.16 g (0.26 mmol) of Boc-amino ketone from step C in 2 mL CH$_2$Cl$_2$ at 0° C. was treated with 2 mL TFA. The reaction was stirred at 0° C. for 10 min. The solvents were removed in vacuo and the residue was purified by reverse phase HPLC. Lyophilization provided the desired amino ketone. LCMS (M+H)=514.2. ¹H NMR (CD₃OD) δ 7.33–7.24 (m, 5H), 7.19–7.16 (m, 3H), 4.78 (m, 1H), 3.86 (m, 2H), 3.14 (m, 2H), 2.91 (s, 6H), 2.70 (m, 2H), 1.18 (t, 1H), 1.09 (d, J=6.0 Hz, 3H), 1.00 (m, 2H), 0.86 (m, 4H), 0.53 (m, 1H), 0.38 (m, 1H).

EXAMPLE 7

[CIS (RS, SR)], S

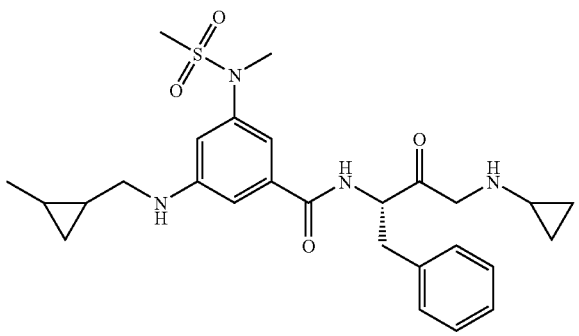

Step A. A solution containing 0.32 g (1.3 mmol) of the intermediate IV, 0.33 g (2.5 mmol) of 1-bromo-2-butyne, and 0.35 g (2.5 mmol) K₂CO₃ in 12.5 mL of acetonitrile was heated at reflux for 4 h. The reaction mixture was cooled and diluted with 60 mL of H₂O. The mixture was extracted with of EtOAc (3×60 mL). The combined organics were washed with brine (60 mL) then dried (MgSO₄). The solvent was removed in vacuo and purified by silica gel chromatography (20%–50% EtOAc:Hex) to afford alkynyl aniline. LCMS (M+H)=311.2.

Step B. A solution containing 0.083 g (0.27 mmol) of alkynyl aniline from step A in 3 mL MeOH was treated with a catalytic amount of Lindlar's catalyst and stirred at room temperature under a hydrogen atmosphere for 10 min. The reaction was filtered through plug of silica gel and the solvent was removed in vacuo. Purification by reverse phase HPLC afforded Z-alkenyl aniline. LCMS (M+H)=313.2.

Step C. A solution containing 0.038 g (0.12 mmol) Z-alkenyl aniline from step B in 2.5 mL EtOAc at 0° C. was treated with 0.058 g (1.3 mmol) of freshly prepared diazomethane and a catalytic amount of palladium(II) acetate and stirred at 0° C. for 15 min. The reaction was filtered through a plug of silica gel. Evaporation of the solvent left the methyl cyclopropyl methyl aniline. LCMS (M+H)= 327.2.

Step D. To 0.034 g (0.10 mmol) of the methyl cyclopropyl methyl aniline from step C in 5 mL THF:MeOH (1:1) was added 2 N NaOH (0.15 mL, 0.30 mmol). The solution was heated to 50° C. for 1 h. After cooling the solution was acidified by the addition of 1 N HCl (20 mL) and extracted with EtOAc (3×30 mL). The combined organic extracts were dried over MgSO₄, filtered, and concentrated in vacuo to the desired carboxylic acid. LCMS (M+H)=313.2.

Step E: A solution containing 0.020 g (0.060 mmol) of the carboxylic acid from step D in 10 mL of CH₂Cl₂ was treated sequentially with BOP reagent (0.026 g, 0.060 mmol), the amine from intermediate III (0.018 g, 0.060 mmol), and diisopropylethylamine (0.023 g, 0.180 mmol). The reaction mixture was stirred at ambient temperature for 30 minutes. Evaporation of the solvent and purification with reverse phase HPLC afforded the amide. LCMS (M+H)=515.3. ¹H NMR (CD₃OD) δ 7.27 (m, 4H), 7.16 (m, 1H), 7.15–6.91 (m, 3H), 4.22 (m, 1H), 4.01 (m, 1H), 3.27 (m, 2H), 3.20–3.06 (m, 2H), 2.90 (s, 3H), 2.89 (s, 3H), 2.87–2.75 (m, 2H), 2.02 (d, J=7.7, 3H), 1.71 (m, 1H), 1.24 (t, 2H), 1.06 (m, 2H), 0.99–0.87 (m, 4H).

Step F. A solution containing 0.051 g (0.10 mmol) of the amide from step E, 0.026 g (0.12 mmol) of di-tert-butyl dicarbonate, and 0.016 g (1.2 mmol) of DIPEA was stirred in 1 mL of ACN at 50° C. for 1.5 h. The reaction mixture was cooled and the solvent was removed in vacuo to afford the Boc amine. LCMS (M+H)=615.3.

Step G. A solution containing 0.062 g (0.10 mmol) of the Boc amine from step F in 1 mL CH₂Cl₂ at 0° C. was treated with 0.042 g (0.10 mmol) of Dess-Martin periodinane. The reaction mixture was warmed to room temperature and stirred for 1 h. The solvent was removed in vacuo and the residue was purified by reverse phase HPLC. Lyophilization provided the Boc-amino ketone. LCMS (M−Boc)=513.3.

Step H. A solution containing 0.0080 g (0.013 mmol) of Boc-amino ketone from step G in 1 mL CH₂Cl₂ at 0° C. was treated with 1 mL TFA. The reaction was stirred at 0° C. for 10 min. The solvents were removed in vacuo to afford the desired amino ketone. LCMS (M+H)=513.3. ¹H NMR (CD₃OD) δ 7.35–7.24 (m, 5H), 7.04 (m, 2H), 6.94 (m, 1H), 4.76 (m, 1H), 4.39 (m, 2H), 4.05 (m, 2H) 3.29 (s, 3H), 3.22–3.04 (m, 2H), 2.92 (s, 3H), 2.74 (m, 2H), 1.76 (m, 2H), 1.29 (m, 3H), 1.12 (m, 1H), 0.97–0.85 (m, 4H).

EXAMPLE 8

[TRANS (RR, SS)], S

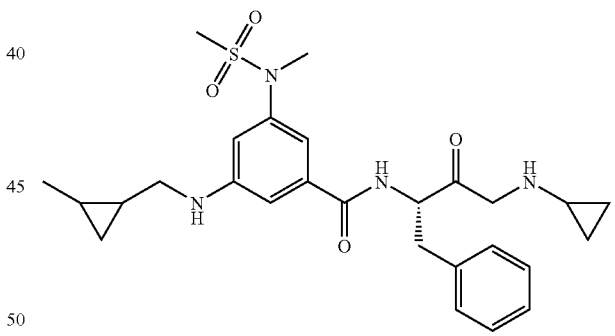

Step A. A solution containing 0.14 g (0.53 mmol) of intermediate IV, 0.072 g (0.53 mmol) of trans-crotyl bromide, and 0.073 g (0.53 mmol) K₂CO₃ in 5 mL of acetonitrile was heated at reflux for 2 h. The reaction mixture was cooled and diluted with 12 mL of H₂O. The mixture was extracted with 3×12 mL of EtOAc. The combined organics were washed with brine (12 mL) before being dried (MgSO₄). The solvent was removed in vacuo and purified by silica gel chromatography (20%–50% EtOAc:Hex) to afford the alkenyl aniline. LCMS (M+H)=313.2.

Step B. A solution containing 0.064 g (0.21 mmol) alkenyl aniline from step A in 7 mL EtOAc at 0° C. was treated with 0.18 g (4.1 mmol) of freshly prepared diazomethane and a catalytic amount of palladium(II) acetate and stirred at 0° C. for 15 min. The reaction was filtered through a plug of silica gel. Evaporation of the solvent left the methyl cyclopropyl methyl aniline. LCMS (M+H)=327.2.

Step C. To 0.067 g (0.21 mmol) of the methyl cyclopropyl methyl aniline from step C in 5 mL THF:MeOH (1:1) was added 2 N NaOH (0.31 mL, 0.63 mmol). The solution was heated to 50 C for 1 h. After cooling the solution was acidified by the addition of 1 N HCl (20 mL) and extracted with EtOAc (3×30 mL). The combined organic extraction were dried over MgSO$_4$, filtered, and concentrated in vacuo to yield of the desired carboxylic acid. LCMS (M+H)=313.2.

Step D: A solution containing 0.032 g (0.10 mmol) of the carboxylic acid from step C in 10 mL of CH$_2$Cl$_2$ was treated sequentially with BOP reagent (0.043 g, 0.10 mmol), the amine from intermediate m (0.029 g, 0.10 mmol), and diisoptopylethylamine (0.039 g, 0.30 mmol). The reaction mixture was stirred at ambient temperature for 30 minutes. Evaporation of the solvent and purification with reverse phase HPLC afforded the amide. LCMS (M+H)=515.3. $^1$H NMR (CD$_3$OD) δ 7.26 (m, 4H), 7.19–6.89 (m, 4H), 4.23 (m, 1H), 3.98 (m, 1H), 3.63–3.29 (m, 2H), 3.07 (m, 2H), 2.91 (s, 3H), 2.90 (s, 3H), 2.88–2.73 (m, 2H), 1.68 (m, 1H), 1.04 (d, J=6.1, 3H), 0.97–0.87 (m, 4H), 0.45 (m, 2H), 0.32 (m, 2H).

Step E. A solution containing 0.020 g (0.040 mmol) of the amide from step D, 0.010 g (0.050 mmol) of di-tert-butyl dicarbonate, and 0.0060 g (0.050 mmol) of DIPEA was stirred in 1 mL of ACN at 50° C. for 1 h. The reaction mixture was cooled and the solvent was removed in vacuo to afford the Boc amine. LCMS (M–Boc)=515.3.

Step F. A solution containing 0.025 g (0.040 mmol) of the Boc amine from step E in 1 mL CH$_2$Cl$_2$ at 0° C. was treated with 0.034 g (0.080 mmol) of Dess-Martin periodinane. The reaction mixture was warmed to room temperature and stirred for 20 min. The solvent was removed in vacuo and the residue was purified by reverse phase HPLC. Lyophilization provided the Boc-amino ketone. LCMS (M–Boc)=513.3.

Step G. A solution containing 0.0050 g (0.0080 mmol) of Boc-amino ketone from step F in 0.5 mL CH$_2$Cl$_2$ at 0° C. was treated with 0.5 mL TFA. The reaction was stirred at 0° C. for 10 min. The solvents were removed in vacuo to afford the desired amino ketone. LCMS (M+H)=513.3. $^1$H NMR (CD$_3$OD) δ 7.29 (m, 5H), 7.01 (m, 2H), 6.88 (m, 1H), 4.74 (m, 1H), 4.37 (m, 2H), 4.03 (m, 2H), 3.14 (m, 2H), 2.91 (s, 3H), 2.90 (s, 3H), 1.71 (m, 2H), 1.29 (s, 4H), 1.17 (m, 1H), 1.02 (m, 1H), 0.87 (m, 3H), 0.69 (m, 1H).

EXAMPLE 9

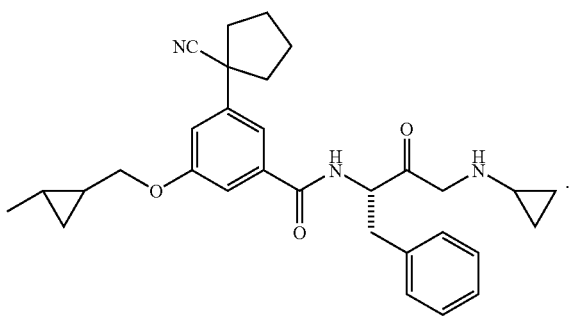

Step A. A solution containing 0.030 g (0.10 mmol) of the carboxylic acid Intermediate V in 5 mL of CH$_2$Cl$_2$ was treated sequentially with BOP reagent (0.043 g, 0.10 mmol), amine Intermediate III (0.029 g, 0.10 mmol), and diisopropylethylamine (0.039 g, 0.30 mmol). The reaction mixture was stirred at ambient temperature for 10 minutes before the solvent was evaporated. The resulting residue was purified by reverse phase HPLC to yield the desired amide.

Step B. A solution containing 0.050 g (0.10 mmol) of the amine from step A, 0.022 g (0.10 mmol) of di-tert-butyl dicarbonate, and 0.012 g (0.10 mmol) of DIPEA was stirred in 1 mL of ACN at 45° C. for 3 h. The reaction mixture was cooled and the solvent was removed in vacuo to afford the Boc amine that was used without further purification.

Step C. A solution containing 0.020 g (0.040 mmol) of the amine from step B in 1 mL CH$_2$Cl$_2$ at 0° C. was treated with 0.034 g (0.080 mmol) of Dess-Martin periodinane. The reaction mixture was warmed to room temperature and stirred for 20 min. The solvent was removed in vacuo and the residue was purified by reverse phase HPLC. Lyophilization provided Boc-amino ketone. This compound was dissolved in EtOAc at 0° C. and treated directly with HCl gas for 5 minutes. The reaction mixture was stirred for 1 h, the solvent was evaporated and the residue was purified by reverse phase chromatography. LCMS (M–Boc)=500.6. $^1$H NMR (CDCl$_3$) δ 7.29 (m, 8H), 5.88 (m, 1H), 5.10 (m, 1H), 4.75 (dd, 1H), (d, 1H), 4.00 (d, 1H), 3.14 (dd, 1H), 2.72 (m, 1H), 2.43 (m, 1H), 2.11 (m, 2H), 1.99 (m, 1H), 1.33 (d, 2H), 0.86 (m, 2H).

EXAMPLE 10

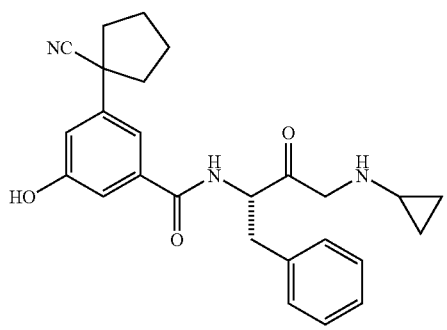

A 0° C. solution containing 30 mg (0.050 mmol) of the aryl ether from Example 9, step B in 5 mL of DCM was treated with 5 mL of TFA. The reaction was allowed to stir for 2 h before the solvents were evaporated and the residue purified using reverse phase chromatography. $^1$H NMR (CDCl$_3$) δ 7.28 (m, 8H), 4.75 (dd, 1H), 4.37 (d, 1H), 4.00 (d, 1H), 3.14 (dd, 1H), 2.72 (m, 1H), 2.43 (m, 2H), 2.11 (m, 2H), 1.99 (m, 2H), 0.86 (m, 2H).

EXAMPLE 11

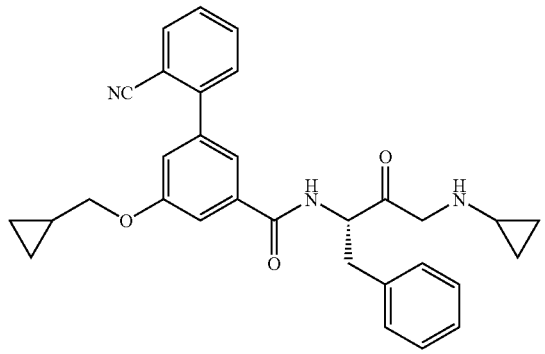

Step A: A solution of methyl 3,5-dihydroxybenzoate (1.00 g, 2.96 mmol) and $K_2CO_3$ (1.6 g, 5.92 mmol) in dry acetone (35 mL) was treated with (bromomethyl)cyclopropane (0.40 g, 2.96 mmol). The mixture was refluxed for 12 h. After cooling, the solution was made acidic with 1N HCl and extracted with EtOAc (3×50 mL). The combined organic layers were dried over $MgSO_4$, filtered and concetrated. Purification by silica gel chromatography (20% EtOAc/Hexanes) provided the mono phenol. LCMS (M+H)=223.2. $^1$H NMR ($CDCl_3$) δ 7.16 (s, 1H), 7.13 (s, 1H), 6.64 (s, 1H), 6.13 (s, 1H), 3.90 (s, 3H)m 3.81 (d, J=6.9 Hz, 2H), 1.23 (m, 1H), 0.65 (m, 2H), 0.34 (m, 2H)

Step B: To a –78° C. solution of the phenol (0.63 g, 2.8 mmol) from step 1 in dichloromethane (20 mL) was added DIPEA (0.4 g, 3.1 mmol) followed by triflic anhydride (0.87 g, 3.1 mmol). The solution was allowed to warm slowly to RT over 12 h after which the reaction was quenched by the addition of saturated sodium bicarbonate (20 mL). The organic layer was seperated and washed sequentially with 1N HCl (1×20 mL), $H_2O$ (1×20 mL), and brine (1×20 mL). The organic layer was dried over $MgSO_4$, filtered and concentrated in vacuo. Purification by silica gel chromatography (10% EtOAc/Hexanes) provided the triflate. $^1$H NMR ($CDCl_3$) δ 7.58 (s, 1H), 7.50 (s, 1H), 7.01 (s, 1H), 3.94 (s, 3H), 3.88 (d, J=7.0 Hz, 2H), 1.28 (m, 1H), 0.69 (m, 2H), 0.39 (m 2H).

Step C: A solution of the triflate from step 2 (0.30 g, 0.85 mmol), $CsCO_3$ (0.42 g, 1.28 mmol), and 2-cyanoarylboronic acid (0.22 g, 1.0 mmol) was degassed under vacuum. $Pd(PPh_3)_4$ (0.98 g, 0.09 mmol) was then added and the reaction mixture was heated to 90° C. for 1 h. Water (60 mL) was added followed by extraction with EtOAc (3×30 mL). The combined organic layers were dried over $MgSO_4$, filtered, and concetrated in vacuo. Purification by silica gel chromatography (10% EtOAc/Hexanes) provided the biarylester. LCMS (M+H)=308.3. $^1$H NMR ($CDCl_3$) δ 7.78–7.31 (m 7H), 3.93 (s, 3H), 3.92 (d, J=7.0 Hz, 2H), 1.28 (m 1H), 0.68 (m 2H), 0.38 (m, 2H).

Step D. A solution of 0.036 g (0.12 mmol) of ester from step 3 in 2 mL of a 1:1 mixture of THF:MeOH was treated with 0.18 mL 2N NaOH. The reaction mixture was stirred for 1 h at 50° C. then cooled to room temperature. The reaction was quenched to a pH=2 with 1N HCl. The mixture was extracted with 3×25 mL of EtOAc. The combined organics were washed with water (20 mL) and brine (20 mL) before being dried ($MgSO_4$). Evaporation of the solvent afforded the carboxylic acid. LCMS (M+1)=294.13.

Step E. A solution containing 0.083 g (0.28 mmol) of acid from step 4, 0.12 g (0.42 mmol) of amine 1, 0.12 g (0.28 mmol) of BOP reagent, and 0.11 g (0.84 mmol) of N,N-diisopropylethylamine in 3 mL $CH_2Cl_2$ was stirred at room temperature for 12 h. The solvent was removed in vacuo and the residue was purified by reverse phase HPLC. Lyophilization provided the hydroxylamine. LCMS (M+1)=496.14. $^1$H NMR ($CD_3OD$) δ 7.83 (d, J=7.7, 1H), 7.75 (t, 1H), 7.55 (t, 2H), 7.37 (s, 1H), 7.31–7.23 (m, 6H), 7.18–7.15 (t, 1H), 4.6 (m, 1H), 4.0 (m, 1H), 3.89 (d, J=6.9, 2H), 3.34 (m, 2H), 3.18 (m, 1H), 2.84 (m, 1H), 2.76 (m, 1H), 1.31–1.23 (m, 1H), 0.97–0.86 (m, 4H), 0.63 (d, J=8.1, 2H), 0.37 (d, J=4.8).

Step F. A solution containing 0.14 g (0.28 mmol) of amine from step 5, 0.074 g (0.34 mmol) of di-tert-butyl dicarbonate, and 0.060 g (0.34 mmol) of DIPEA was stirred in 6 mL of ACN at 50° C. for 1 h. The reaction mixture was cooled and the solvent was removed in vacuo to afford the Boc protected amine. LCMS (M+1–100)=496.09.

Step G. A solution containing 0.17 g (0.28 mmol) of the Boc protected amine from step 6 in 2 mL $CH_2Cl_2$ at 0° C. was treated with 0.24 g (0.56 mmol) of Dess-Martin periodinane. The reaction mixture was warmed to room temperature and stirred for 30 min. The solvent was removed in vacuo and the residue was purified by reverse phase HPLC. Lyophilization provided the desired Boc protected aminoketone. LCMS (M+1–100)=494.09.

Step H. A solution containing 0.11 g (0.19 mmol) of ketone from step 7 in 2 mL CH2Cl2 at 0° C. was treated with 2 mL TFA. The reaction was stirred at 0° C. for 10 min. then room temperature for 10 min. The solvents were removed in vacuo and the residue was purified by reverse phase HPLC. Lyophilization provided the desired amino-ketone. LCMS (M+1)=494.11. $^1$H NMR ($CD_3OD$) δ 7.83 (d, J=7.7, 1H), 7.74 (t, 1H), 7.56 (m, 2H), 7.50 (s, 1H), 7.36 (s, 1H), 7.30 (m, 5H), 7.23 (m, 1H), 4.80 (dd, J=5.5, 9.2, 1H), 4.41 (d, J=17.9, 1H), 4.08 (d, J=17.8, 1H), 3.91 (d, J=17.0, 2H), 3.37–3.28 (m, 1H), 3.14 (m, 1H), 2.72 (m, 1H), 1.32–1.25 (m, 1H), 0.90–0.82 (m, 4H), 0.93 (d, J=8.1, 2H), 0.37 (d, J=4.8).

EXAMPLE 12

R, S, R, R Diastereomer

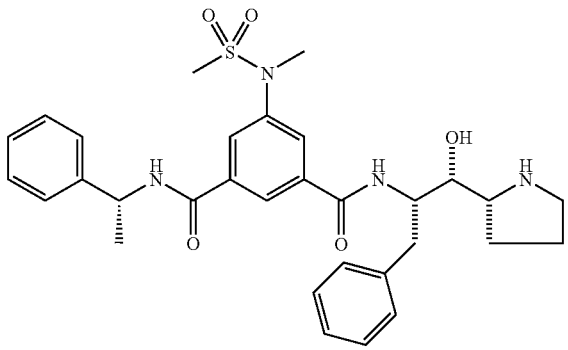

Step A. To a –70° C. solution containing 2.57 g (15.01 mmol) of N-Boc-4-pyrrolidine in 75 mL of ether was added 1.4 M sec-BuLi (11.8 ml, 16.5 mmol). The resulting reaction mixture was stirred at this temperature for 4 h then treated with 4.94 g (15.01 mmol) of N,N-dibenzyl-L-phenylalanal in 20 mL of ether. The reaction was complete within 5 minutes. The reaction mixture was quenched with 50 mL of saturated NaHCO₃ and extracted with EtOAc (3×50 mL). The combined organic extracts were washed with water and brine (2×25 mL). Evaporation of the solvent and column chromatography (1:4 EtOAc/Hexanes) separated the (S, R, R) diastereomer and the (S, R, S) diastereomer.

(S, R, R) Diastereomer: ¹H NMR (CDCl₃) δ 7.34–7.10 (m, 15 H), 4.19 (m, 1H), 3.82–2. (m, 9H), 1.83 (m, 2H), 1.47 (s, 9H), 1.26 (m, 4H). LCMS (M+H)=501.3.

(S, R, S) Diastereomer: ¹H NMR (CDCl₃) δ 7.29 (m, 15 H), 4.96 (m, 1H), 3.96 (d, J=14.5 Hz, 2H), 3.78 (m 1H), 3.56 (d, J=14.5 Hz, 2H), 3.33 (m, 3H), 3.07 (m, 1H), 2.84 (m, 2H), 1.83 (m, 4H), 1.47 (s, 9H). LCMS (M+H)=501.3

Step B. A solution containing 0.130 g (0.259 mmol) of the (S, R, R) dibenzylamine from step A and a catalytic amount of 10% Pd(OH)₂ in 5 mL of MeOH was hydrogenated under a balloon of hydrogen gas for 16 h. The mixture was filtered through a pad of Celite and evaporated to give the desired amine as an oil. LCMS (M+H)=321.3

Step C. A solution containing 92 mg (0.24 mmol) of the intermediate acid I in 5 mL of CH₂Cl₂ was treated sequentially with BOP reagent (103 mg, 0.24 mmol), the (S, R, R) amine from step B (78 mg, 0.24 mmol), and diisopropylethylamine (0.13 mL, 0.72 mmol). The reaction mixture was stirred at ambient temperature for 30 minutes. Evaporation of the solvent and purification with reverse phase HPLC gave the amide. LCMS (M+H)=679.3.

Step D. A solution containing 73 mg (0.108 mmol) of the Boc-protected amine from step C in 6 mL CH₂Cl₂:TFA (4:1) was stirred 45 min at ambient temperature. The reaction was cooled, evaporated and purified by reverse phase HPLC to afford the desired compound as its TFA salt. (S, R, R) Diastereomer: ¹H NMR (CD₃OD) δ 8.86 (d, J=7.3 Hz, 1H), 8.42 (d, J=9.0 Hz, 1H), 7.97 (s, 2H), 7.74 (s, 1H), 7.40–7.10 (m, 10H), 5.22 (q, J=7.1 Hz, 1H), 4.18 (m, 1H), 4.04 (dd, J=9.4, 2.2 Hz, 1H), 3.74 (t, J=7.0 Hz, 1H), 3.40–3.26 (m, 2H), 3.33 (s, 3H), 2.94 (s, 3H), 2.81 (t, J=11.0 Hz, 1H), 2.19–2.07 (m, 2H), 2.01 (m, 1H), 1.57 (d, J=7.0 Hz, 3H). LCMS (M+H)=579.2

EXAMPLE 13

R, S, R, S Diastereomer

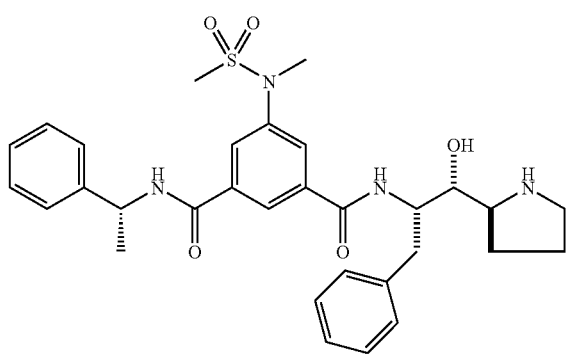

Step A. A solution containing 146 mg (0.39 mmol) of the intermediate acid I in 5 mL of CH₂Cl₂ was treated sequentially with BOP reagent (164 mg, 0.39 mmol), the (S, R, S) amine from Example 12, step B (150 mg, 0.48 mmol), and diisopropylethylamine (0.21 mL, 1.17 mmol). The reaction mixture was stirred at ambient temperature for 30 minutes. Evaporation of the solvent and purification with reverse phase HPLC gave the amide. LCMS (M+H)=679.3.

Step B. A solution containing 32 mg (0.047 mmol) of the Boc-protected amide from step A in 2.5 mL CH₂Cl₂:TFA (4:1) was stirred 30 min at ambient temperature. The reaction was cooled, evaporated and purified by reverse phase HPLC to provide the desired compound as its TFA salt. ¹H NMR (CD₃OD) δ 8.87 (d, J=8.4 Hz, 1H), 8.47 (d, J=8.4 Hz, 1H), 8.04 (s, 1H), 7.99 (s, 1H), 7.82 (s, 1H), 7.42–7.14 (m, 9H), 7.16 (t, J=7.3 Hz, 1H), 5.24 (q, J=7.0 Hz, 1H), 4.29 (m, 1H), 3.74 (m, 2H), 3.53–3.33 (m, 3H), 3.35 (s, 3H), 2.95 (s, 3H), 2.81 (m, 1H), 2.15 (m, 2H), 2.03 (m 2H), 1.59 (d, J=7.3 Hz, 3H). LCMS (M+H)=579.3.

EXAMPLE 14

R, S, R, R Diastereomer

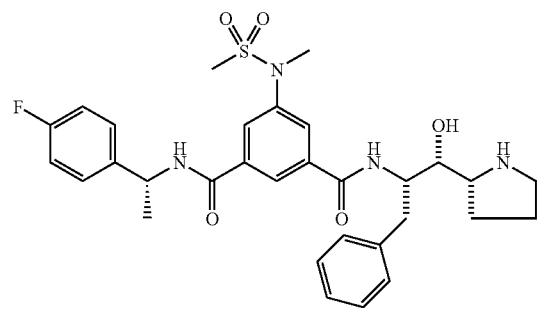

Step A. A solution containing 27 mg (0.069 mmol) of the p-fluoro acid intermediate II in 2 mL of CH₂Cl₂ was treated sequentially with BOP reagent (0.030 mg, 0.069 mmol), the (S, R, R) amine from Example 12, step A (78 mg, 0.24 mmol), and diisopropylethylamine (0.033 mL, 0.188 mmol). The reaction mixture was stirred at ambient temperature for 30 minutes. Evaporation of the solvent and purification by reverse phase HPLC afforded the amide. LCMS (M+H)= 697.2.

Step B. A solution containing 18 mg (0.026 mmol) of the Boc-protected amine from step A in 2 mL CH₂Cl₂:TFA (4:1) was stirred 2 h at ambient temperature. The reaction was cooled, evaporated and purified by reverse phase HPLC to provide the desired compound as its TFA salt. ¹H NMR (CD₃OD) δ 8.86 (m, 1H), 8.43 (d, J=8.2 Hz, 1H), 7.97 (s, 2H), 7.75 (s, 1H), 7.41–7.06 (m, 9H), 5.22 (m, 1H), 4.18 (m, 1H), 4.04 (m 1H), 3.73 (m, 1H), 3.40–3.26 (m, 2H), 3.33 (s, 3H), 2.94 (s, 3H), 2.81 (m, 1H), 2.19–1.99 (m, 3H), 1.56 (d, J=6.1, 3H). LCMS (M+H)=597.2

EXAMPLE 15

R, S, R, R Diastereomer

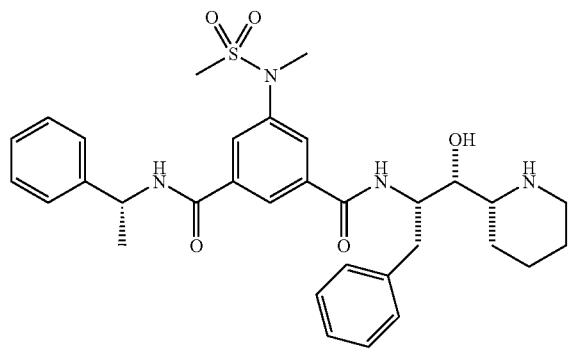

Step A. To a −70° C. solution containing 1.12 g (6.05 mmol) of N-Boc-4-piperidine in 15 mL of ether was added TMEDA (0.77 g, 6.66 mmol) then 1.4 M sec-BuLi (4.76 ml, 6.66 mmol). The resulting reaction mixture was stirred at this temperature for 1 h then, warmed to −20° C. for 10 min, recooled to −70° C. then treated with 2.0 g (6.05 mmol) of N,N-dibenzyl-L-phenylalanal in 5 mL of ether. The reaction was complete within 10 minutes but was allowed to stir to rt over 4 h to effect cyclization of the undesired erythro isomer (e.g see Beak and Lee, J. Org. Chem. 1993, 58, 1109–1117). The reaction mixture was quenched with 50 mL of saturated NaHCO$_3$ and extracted with EtOAc (3×50 mL). The combined organic extracts were washed with water and brine (2×25 mL). Evaporation of the solvent and column chromatography (1:4 EtOAc/Hexanes) afforded the diastereomerically pure alcohol. $^1$H NMR (CDCl$_3$) δ 7.30 (m, 15 H), 4.40 (m, 1H), 4.15 (m, 1H), 3.83 (d, J=14 Hz, 2H), 3.73 (m, 1H), 3.59 (d, J=14 Hz, 2H), 3.10–2.91 (m, 3H), 2.74 (m, 1H), 1.94 (m 1H), 1.67–0.94 (m, 6H), 1.39 (s, 9H). LCMS (M+H)=515.4.

Step B. A solution containing 0.158 g (0.307 mmol) of the dibenzylamine from step A and a catalytic amount of 10% Pd(OH)$_2$ in 10 mL of MeOH was hydrogenated under a balloon of hydrogen gas for 48 h. The mixture was filtered through a pad of Celite and evaporated to give 0.080 g (78%) of the desired amine as an oil. LCMS (M+H)=335.3.

Step C. A solution containing 90 mg (0.24 mmol) of the intermediate acid I in 5 mL of CH$_2$Cl$_2$ was treated sequentially with BOP reagent (101 mg, 0.24 mmol), the amine from step B (80 mg, 0.24 mmol), and diisopropylethylamine (0.13 mL, 0.72 mmol). The reaction mixture was stirred at ambient temperature for 30 minutes. Evaporation of the solvent and purification by silica gel chromatography (100% EtOAc) afforded the amide. $^1$H NMR (CDCl$_3$) δ 7.93–7.10 (m, 14 H), 6.77 (d, J=7.4 Hz, 1H), 5.26 (m, 1H), 4.41 (m, 1H), 4.32 (m, 1H), 4.07 (m, 1H), 3.28 (s, 3H), 3.08 (m, 1H), 2.89 (s, 3H), 2.95–2.71 (m, 2H), 2.15 (m 1H), 1.73–1.43 (m, 7H), 1.59 (d, J=7.0 Hz, 3 H), 1.51. (s, 91) LCMS (M−BOC)= 593.3.

Step D. A solution containing 34 mg (0.05 mmol) of the Boc protected amine from step C in 2.5 mL CH$_2$Cl$_2$:TFA (4:1) was stirred 15 min at ambient temperature. The reaction was cooled, evaporated and purified by reverse phase HPLC to afford the desired compound as its TFA salt. $^1$H NMR (CD$_3$OD) δ 8.87 (d, J=7.3 Hz, 1H), 8.39 (d, J=9.1 Hz, 1H), 7.98 (s, 2H), 7.76 (s, 1H), 7.42–7.11 (m, 10 H), 5.24 (q, J=7.0 Hz, 1H), 4.23 (m, 1H), 3.91 (d, J=8.0 Hz, 1H), 3.33 (m, 1H), 3.34 (s, 3H), 3.22 (d, J=12 Hz, 1H), 3.04 (m, 1H), 2.95 (s, 3H), 2.82 (m, 1H), 2.17 (d, J=12 Hz, 1H), 1.95–1.45 (m, 5H), 1.58 (d, J=7.0 Hz, 3H). LCMS (M+H)=593.3.

EXAMPLE 16

R, S, R, R Diastereomer

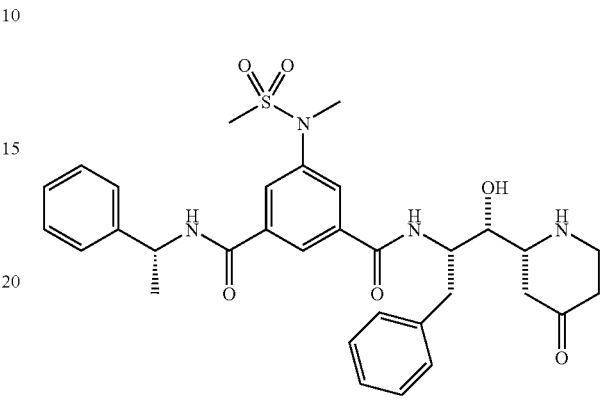

Step A. To a −70° C. solution containing 3.28 g (13.6 mmol) of N-Boc-4-piperidone ethylene ketal in 30 mL of ether was added TMEDA (1.91 g, 16.4 mmol) then 1.4 M sec-BuLi (12.6 ml, 16.4 mmol). The resulting reaction mixture was stirred at this temperature for 4 h then treated with 5.4 g (16.4 mmol) of N,N-dibenzyl-L-phenylalanal in 25 mL of ether. The reaction was complete within 10 minutes but was allowed to stir to rt over 4 h to effect cyclization of the undesired erythro isomer (e.g see Beak and Lee, J. Org. Chem. 1993, 58, 1109–1117). The reaction mixture was quenched with 50 mL of saturated NH$_4$Cl and diluted with 100 mL of ether. The organic phase was separated and washed with water and brine (2×25 mL). Evaporation of the solvent and column chromatography (1:4 EtOAc/Hexanes) afforded the diastereomerically pure alcohol. $^1$H NMR (CDCl$_3$) δ 7.38–6.95 (m, 15H), 4.41 (bs, 1H), 4.00–3.80 (m, 8H), 3.53 (m, 2H), 3.22 (bt, 1H), 3.10–2.80 (m, 2H), 2.00–1.60 (m, 5H), 1.25 (s, 9H). LCMS (M+H)= 573.38.

Step B. A solution containing 3.2 g (5.5 mmol) of the dibenzylamine from step A and 1.5 g of 10% Pd(OH)$_2$ in 100 mL of MeOH was hydrogenated under a balloon of hydrogen gas for 3 h. The mixture was filtered through a pad of Celite and evaporated to give the desired amine as an oil. $^1$H NMR (CDCl$_3$) δ 7.31–7.22 (m, 5H), 4.48 (bs, 1H), 4.16 (d, J=9.5 Hz, 1H), 4.20–3.89 m, 4H), 3.21–3.05 (m, 2H), 2.81–2.51 (m, 2H), 2.47 (t, J=11.2 Hz, 1H), 2.24 (d, J=14 Hz, 1H), 1.71 (dd, J=14, 6.4 Hz, 1H), 1.65 (m, 2H), 1.47 (s, 9H). LCMS (M+H)=393.32.

Step C. A solution containing 37.7 mg (0.100 mmol) of the intermediate acid I in 1 mL of DMF was treated sequentially with BOP reagent (44.2 mg, 0.100 mmol), the amine from step B (39.3 mg, 0.1 mmol), and diisopropylethylamine (0.042 mL, 0.240 mmol). The reaction mixture was stirred at ambient temperature for ten minutes. Evaporation of the solvent and purification by reverse phase HPLC afforded the desired ketal that was used without further purification.

Step D. A solution containing 37 mg (0.05 mmol) of the ketal from step C in 6 mL of 1:1 THF/3N HCl was heated at 55° C. for 2 h. The reaction was cooled, evaporated to ⅓ volume and purified by reverse phase HPLC to afford the desired compound as its TFA salt. $^1$H NMR (CDCl$_3$ w/0.05% DMSO-d$_6$) δ 8.20 (s, 1H), 8.04 (s, 1H), 7.85 (m, 2H), 7.66 (m, 1H), 7.44–7.15 (m, 10H), 5.30 (m, 1H), 4.25 (m, 2H), 4.11 (m, 1H), 3.77 (m, 1H), 3.58 (m, 1H), 3.21 (m, 1H), 3.30 (s, 3H), 3.20 (m, 1H), 3.11–2.85 (m, 4H), 2.80 (s, 3H), 1.61 (d, J=7 Hz, 3H). LCMS (M+1+H$_2$O)=625.32.

EXAMPLE 17

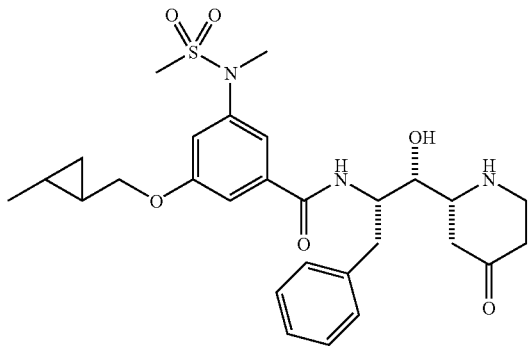

Step A. A solution containing 74.0 mg (0.236 mmol) of the acid from intermediate VI in 2 mL of DMF was treated sequentially with BOP reagent (105 mg, 0.236 mmol), amine from Example 16, step B (93.0 mg, 0.236 mmol), and diisopropylethylamine (0.099 mL, 0.566 mmol). The reaction mixture was stirred at ambient temperature for 15 minutes. Evaporation of the solvent and purification by reverse phase HPLC afforded the title compound that was hydrolyzed directly in the next step. LCMS (M+H)=588.32.

Step B. A solution containing 68.0 mg (0.10 mmol) of the ketal from step A in 2 mL of 1:1 THF/3N HCl was heated at 55° C. for 2 h. The reaction was cooled, evaporated and purified by reverse phase HPLC to afford the desired compound as its TFA salt. $^1$H NMR (CDCl$_3$ w/0.05% DMSO-d6) δ 7.99 (s, 1H), 7.65 (m, 1H), 7.40–7.20 (m, 5H), 7.05 (s, 1H), 4.05 (m, 1H), 3.90 (m, 2H), 3.22 (s, 3H), 2.94 (m, 4H), 2.80 (s, 3H), 2.45 (m, 1H), 2.11 (m, 1H), 1.80 (m, 1H), 1.55 (m, 1H), 1.22 (m, 1H), 1.10 (bs, 3H), 0.95 (m, 1H), 0.75 (m, 1H), 0.51 (m, 1H), 0.35 (m, 1H). LCMS (M+1)=544.29.

EXAMPLE 18

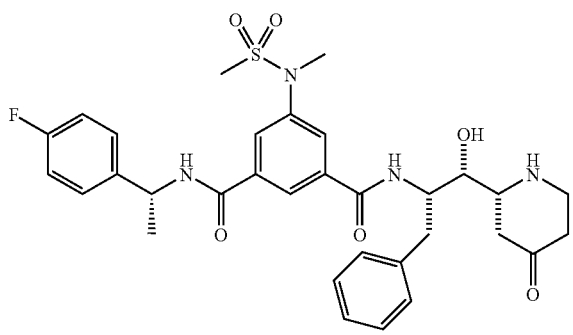

Example 18 was prepared in a manner similar to Example 16 steps A-D using carboxylic acid II. $^1$H NMR (CD$_3$OD) δ 8.85 (d, 1H), 8.40 (d, 1H), 7.99 (s, 2H), 7.66 (s, 1H), 7.44–7.00 (m, 9H), 5.20 (m, 1H), 4.25 (m, 1H), 4.11 (m, 1H), 3.59 (m, 1H), 3.52 (m, 5H), 3.11 (m, 1H), 2.98 (s, 3H), 2.80 (t, 1H), 2.31 (d, 1H), 2.08 (d, 1H), 1.85 (m, 2H), 1.65 (d, J=7.0 Hz, 3H). LCMS (M+1+H$_2$O) 643.26

EXAMPLE 19

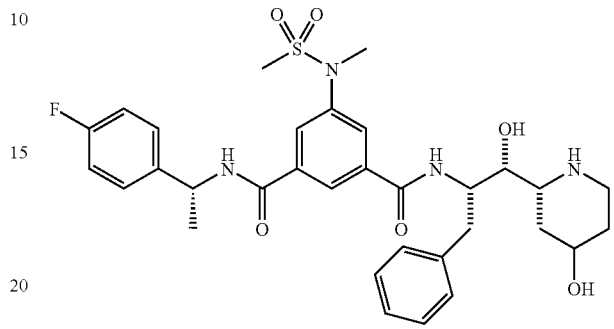

A solution containing 10.0 mg (0.013 mmol) of Example 18 in 1 mL of MeOH was treated with 3.7 mg (0.10 mmol) of NaBH$_4$. After stirring for 2 min the mixture was chromatographed by reverse phase HPLC to afford the desired alcohol. LCMS (M+1)=627.24.

EXAMPLE 20

R, S, S, R Diastereomer

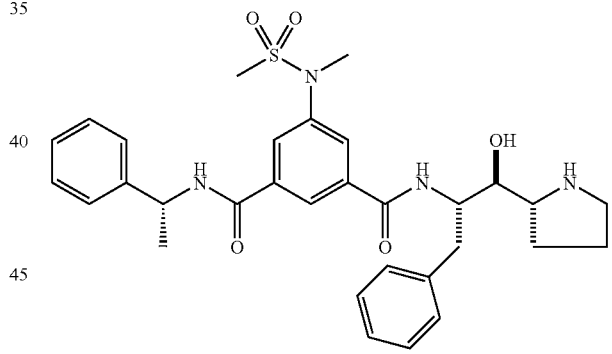

Step A. To 102 mg (0.150 mmol) of the Boc-protected amine from Example 12, step C dissolved in 5 mL CH$_2$Cl$_2$ was added Dess-Martin periodinane (0.191 g, 0.450 mmol) and the solution was stirred at ambient temperature for 1 h. Purification by silica gel chromatography (80% EtOAc) gave the Boc-protected amino ketone. LCMS (M+H)=677.2.

Step B: To a 0° C. solution of 42 mg (0.062 mmol) of the Boc-protected amino ketone in 2 mL ethanol was added sodium borohydride (4 mg, 0.093 mmol). The reaction was stirred for 30 min and purified by reverse phase HPLC to give a 4.3:1 mixture of alcohol diastereomer (S:R). The (S, S, R) Boc-protected amino alcohol was treated with 2.5 mL CH$_2$Cl$_2$:TFA (4:1) and stirred 30 min at ambient temperature. The reaction was evaporated and purified by reverse phase HPLC to afford the desired compound as its TFA salt. $^1$H NMR (CD$_3$OD) δ 8.87 (d, J=6.5 Hz, 1H), 8.31 (d, J=8.9 Hz, 1H), 8.07 (s, 1H), 8.00 (s, 1H), 7.86 (s, 1H), 7.41–7.15 (m, 10H), 5.24 (q, J=6.3 Hz, 1H), 4.44 (m, 1H), 3.79 (d, J=9.0 Hz, 1H), 3.51 (m 1H), 3.35 (s, 3H), 3.23 (t, J=7.1 Hz, 1H), 3.03 (d, J=7.7 Hz, 1H), 2.96 (s, 3H), 2.31 (m, 1H), 1.99 (m, 2H), 1.71 (m, 1H), 1.58 (d, J=7.0 Hz, 3H). LCMS (M+H)=579.3.

EXAMPLE 21

R, S, R, S Diastereomer

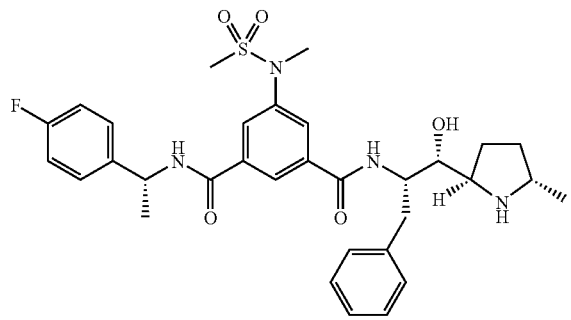

Step A. To a stirred mixture of 1.1 g (6.1 mmol) of (S)-N-Boc-2-pyrrolidine (Donner, B. G. *Tetrahedron Letters* 1995, 36, 1223–1226) and 0.70 g (6.08 mmol) N,N,N',N'-tetramethylethylenediamine in 12 mL of ether at −78° C., 5.2 mL of 1.4M sec-butyllithium was added dropwise. The reaction mixture was stirred at −78° C. for 40 min. A solution of the N,N-dibenzyl-L-phenylalanal in 6 mL ether was then added to the reaction mixture. The reaction was warmed to room temperature over 16 h. The reaction was quenched with 100 mL of saturated bicarb and the mixture was extracted with EtOAc (3×50 mL). The combined organics were washed with brine (100 mL) before being dried over MgSO$_4$, filtered, and concentrated in vacuo. The residue was purified by silica gel chromatography (5%–60% EtOAc:Hex). The isolated product was then purified by reverse phase HPLC. Lyophilization provided the dibenzylamine. $^1$H NMR (CD$_3$OD) δ 8.87 (s, 1H), 8.10 (s, 1H), 7.91 (s, 1H), 7.77 (d, J=7.7 Hz, 1H), 7.65–7.14 (m, 13 H), 5.24 (m, 1H), 4.21 (m, 1H), 3.97 (m, 1H), 3.21 (m, 1H), 2.78 (m, 2H), 2.28 (m, 1H), 2.26 (s, 3H), 1.56 (d, J=7.1 Hz, 3H), 0.91 (m, 4H). LCMS (M+H)=515.4.

Step B. A solution containing 0.031 g (0.060 mmol) of the amine from step A in 1 mL MeOH was treated with a catalytic amount of Pearlman's catalyst and stirred at room temperature under a hydrogen atmosphere for 40 min. The reaction was filtered through plug of celite and the solvent was removed in vacuo. LCMS (M+H)=335.4.

Step C. A solution containing 22 mg (0.055 mmol) of the intermediate acid I in 3 mL of CH$_2$Cl$_2$ was treated sequentially with BOP reagent (24 mg, 0.055 mmol), the (S, R, R) amine from step B (20 mg, 0.055 mmol), and diisopropylethylamine (0.03 mL, 0.167 mmol). The reaction mixture was stirred at ambient temperature for 30 minutes. Evaporation of the solvent and purification reverse phase HPLC to afford the amide. LCMS (M+H)=711.3.

Step D. A solution containing 9 mg (0.013 mmol) of the amide from step C in 1 mL CH$_2$Cl$_2$ at 0° C. was treated with 1 mL TFA. The reaction was stirred at 0° C. for 10 min. The solvents were removed in vacuo to afford the desired amino alcohol. LCMS (M+H)=611.3. $^1$H NMR (CD$_3$OD) δ 8.89 (d, J=7.5 Hz, 1H), 8.43 (d, J=8.8 Hz, 1H), 7.98 (m, 2H), 7.76 (m, 1H), 7.42 (m, 2H), 7.23 (m, 5H), 5.23 (m, 1H), 4.20 (m, 1H), 4.03 (m, 1H), 3.83 (m, 1H), 3.73 (m, 1H), 2.95 (s, 3H), 2.94 (s, 3H), 2.81 (m, 2H), 2.21 (d, J=7.0 Hz, 3H), 1.57 (m, 4H), 1.39 (d, J=6.6 Hz, 3H).

EXAMPLE 22

[CIS (RS, SR)], S, R, R

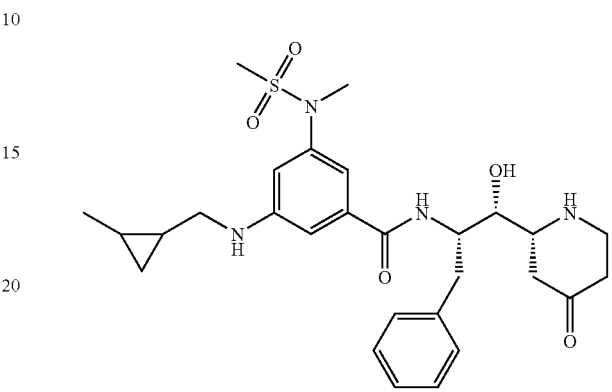

Step A. A solution containing 0.41 g (1.6 mmol) of intermediate IV, 0.21 g (1.6 mmol) of 1-bromo-2-butyne, and 0.22 g (1.6 mmol) K$_2$CO$_3$ in 15 mL of acetonitrile was heated at reflux for 3 h. The reaction mixture was cooled and diluted with 60 mL of H$_2$O. The mixture was extracted with EtOAc (3×60 mL). The combined organics were washed with brine (60 mL) before being dried (MgSO$_4$). The solvent was removed in vacuo and purified by silica gel chromatography (20%–50% EtOAc:Hexanes) to afford the alkylated aniline. LCMS (M+H)=311.2.

Step B. A solution containing 0.19 g (0.62 mmol) of aniline from step A in 5 mL of MeOH was treated with a catalytic amount of Lindlar's catalyst and stirred at room temperature under a hydrogen atmosphere for 20 min. The reaction was filtered through plug of silica gel and the solvent was removed in vacuo. Purification by reverse phase HPLC afforded the Z-alkenyl aniline. LCMS (M+)=313.2.

Step C. A solution containing 0.17 g (0.55 mmol) the alkenyl aniline from step B in 17 mL EtOAc at 0° C. was treated with 0.49 g (11 mmol) of freshly prepared diazomethane and a catalytic amount of palladium(II) acetate and stirred at 0° C. for 15 min. The reaction was filtered through a plug of silica gel. Evaporation of the solvent afforded the methyl cyclopropyl methyl aniline. LCMS (M+H)=327.2.

Step D. 0.17 g (0.52 mmol) of the methyl cyclopropyl methyl aniline from step C was dissolved in 6 mL MeOH:THF (1:1) and 0.78 mL (1.56 mmol) 2N NaOH was added. The reaction mixture was heated to 50° C. for 1 hour. The solution was cooled, acidified with 1N HCl (10 mL) and extracted with EtOAc (3×30 mL). The combined organic extracts were dried over MgSO$_4$, filtered and concentrated in vacuo to afford the carboxylic acid. LCMS (M+H)=313.2.

Step E. A solution containing 0.071 mg (0.23 mmol) of the acid from step D in 3 mL of CH$_2$Cl$_2$ was treated sequentially with BOP reagent (0.097 g, 0.23 mmol), the amine from step B (0.091 g, 0.23 mmol), and diisopropylethylamine (0.089 g, 0.69 mmol). The reaction mixture was stirred at ambient temperature for 30 minutes. Evaporation of the solvent and purification by reverse phase HPLC afforded the amide. LCMS (M+H)=687.3

Step F. A solution containing 0.038 g (0.055 mmol) of amide from step E in 2 mL THF was treated with 1.7 mL 3N HCl. The reaction was stirred at 55° C. for 1 h. The reaction was cooled and the solvents were removed in vacuo. Purification by reverse phase HPLC gave the desired piperidinone. $^{1}$H NMR (CD$_{3}$OD) δ 7.23 (m, 4H), 7.15 (m, 1H), 7.04–6.89 (m, 3H), 4.09 (m, 1H), 4.00 (m, 1H), 3.52–3.45 (m, 4H), 3.35 (s, 3H), 3.34 (s, 3H), 3.31 (m, 2H), 3.25 (2H), 2.97 (m, 1H), 2.87 (m, 2H), 1.23 (m, 1H), 1.20–1.14 (m 5H), 1.07 (m, 1). LCMS (M+H)=543.3.

EXAMPLE 23

CIS, S, R, R

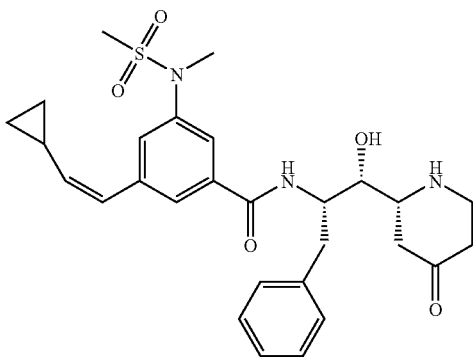

Step A. A solution containing 2.36 g (8.21 mmol) of the acid from intermediate I step C in 15 mL of CHCl$_{3}$ was treated sequentially with BOP reagent (3.63 g, 8.21 mmol), N,O-Dimethylhydroxylamine hydrochloride (0.96 g, 9.85 mmol), and diisopropylethylamine (6.43 mL, 36.9 mmol). The reaction mixture was stirred at ambient temperature for 15 minutes. Evaporation of the solvent and purification by silica gel chromatography (5% MeOH/CHCl$_{3}$) afforded the desired N-methoxy-N-methyl amide. $^{1}$H NMR (CDCl$_{3}$) δ 8.30–8.28 (m, 1 H), 8.11–8.08 (m, 1H), 7.94–7.92 (m, 1H), 3.94 (s, 3H), 3.58 (s, 3H), 3.38 (s, 3H), 3.37 (s, 3H), 2.88 (s, 3H). LCMS (M+H)=331.0.

Step B. To a solution of the Weinreb amide from step A (1.30 g, 3.93 mmol) in 10 mL of THF at −78° C. was added DIBAL-H (4.52 mL, 4.52 mmol) dropwise. The solution stirred for 1 hour at −78° C. and was quenched with MeOH (5 ml) and H$_{2}$O (5 mL). 2N HCl was added and the layers were separated. The aqueous phase was extracted with ether (3×25 mL) and the combined organic extracts were washed with saturated NaHCO$_{3}$ and brine. The solvents were dried over MgSO$_{4}$, filtered and concentrated in vacuo to provide the crude aldehyde. $^{1}$H NMR (CDCl$_{3}$) δ 10.0 (s, 1 H), 8.45–8.43 (m, 1H), 8.29–8.27 (m, 1H), 8.10–8.08 (m, 1H), 3.98 (s, 3H), 3.40 (s, 3H), 2.89 (s, 3H).

Step C. n-Butyllithium (0.15 mL of 1.6 M solution) was added to a suspension of cyclopropylmethyltriphenylphosphonium bromide (0.080 g, 0.20 mmol) in a 2:1 mixture of THF and ether (3 mL) at 0° C. After stirring for 1 hour at ambient temperature the red solution was cooled to −78° C. and the aldehyde (0.05 g, 0.18 mmol) from step B in THF (1 mL) was added. The resulting solution stirred for twelve hours before the solvents were removed in vacuo. The crude olefin was purified by reverse phase HPLC to afford a 1.65:1 ratio of Z:E isomers. Cis olefin: $^{1}$HNMR (CDCl$_{3}$) δ 8.01 (s, 1H), 7.83–7.81 (m, 1H), 7.72–7.70 (m, 1H), 6.32 (d, J=11.5 Hz, 1H), 5.18 (t, J=10.8 Hz, 1H), 3.93 (s, 3H), 3.36 (s, 3H), 2.86 (s, 3H), 1.88–1.80 (m, 1H), 0.92–0.87 (m, 2H), 0.53–0.49 (m, 2H). Trans olefin: $^{1}$H NMR (CDCl$_{3}$) δ 7.90 (s, 1H), 7.76 (s, 1H), 7.52 (s, 1H), 6.47 (d, J=15.7 Hz, 1H), 5.85 (m, 1H), 3.92 (s, 3H), 3.34 (s, 3H), 2.86 (s, 3H), 1.57–1.50 (m, 1H), 0.87–0.84 (m, 2H), 0.55–0.53 (m, 2H) LCMS (M+H)=310.0.

Step D. 478 mg (1.54 mmol) of the phenethenyl cyclopropane from step C was dissolved in 6 mL MeOH:THF (1:1) and 1.15 mL (2.30 mmol) 2N NaOH was added. The reaction mixture was stirred for 1 hour. The solution acidified with 1N HCl (10 mL) and extracted with EtOAc (3×30 mL). The combined organic extracts were dried over MgSO$_{4}$, filtered and concentrated in vacuo to afford the carboxylic acid which was used without further purification. LCMS (M+H)=296.1.

Step E. A solution containing 0.062 g (0.23 mmol) of the acid from step D in 5 mL of CH$_{2}$Cl$_{2}$ was treated sequentially with BOP reagent (0.093 g, 0.21 mmol), the amine from Example 16, step B (0.10 g, 0.25 mmol), and diisopropylethylamine (0.16 g, 0.95 mmol). The reaction mixture was stirred at ambient temperature for 30 minutes. Evaporation of the solvent and purification by reverse phase HPLC afforded the amide. LCMS (M+1)=670.2

Step F. A solution containing 0.06 g (0.089 mmol) of amide from step E in 1.5 mL THF was treated with 1.5 mL 3N HCl. The reaction was stirred at 55° C. for 1 h. The reaction was cooled and the solvents were removed in vacuo. Purification by reverse phase HPLC gave the desired piperidinone. $^{1}$H NMR (CD$_{3}$OD) δ 7.59–7.47 (m, 2H), 7.43–7.39 (m, 2H), 7.33–7.14 (m, 4H), 6.02 (d, J=11.3 Hz, 1H), 5.05 (t, 1H), 4.38–4.22 (m, 1H), 4.06–3.93 (m, 1H), 3.82–3.40 (m, 1H), 3.05–2.82 (m, 3H), 2.58 (m, 2H), 1.75–1.63 (m, 3H), 1.26–0.94 (m, 6H), 0.58–0.43 (m, 2H). LCMS (M+H)=544.0

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of the formula I:

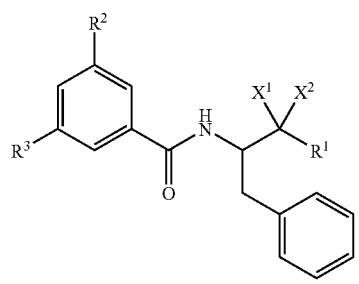

wherein;

$R^1$ is

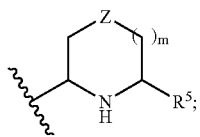

$R^2$ is selected from the group consisting of:
(1) $R^4$—S(O)$_m$—NR$^5$—,
(2) $R^4$—S(O)$_m$—,
(3) $R^4$NHCO—,
(4) $R^4$CONH—,
(5) $R^4R^5$N—,
(6) nitrile,
(7) NC—C$_{1-6}$alkyl—,
(8) halogen, (10)

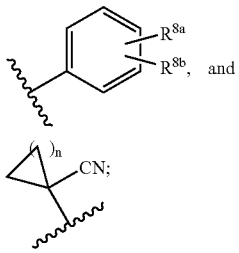

$R^3$ is selected from the group consisting of:

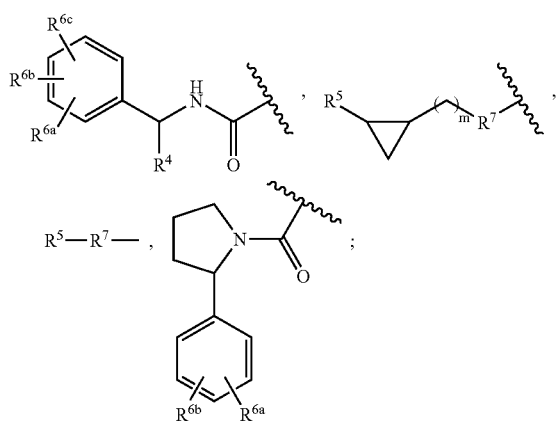

$R^4$ is selected from the group consisting of:
(1) hydrogen,
(2) C$_{1-6}$alkyl,
(3) phenyl, and
(4) benzyl;
$R^5$ is independently selected from the group consisting of:
(1) hydrogen;
(2) C$_{1-6}$alkyl,
(3) phenyl,
(4) benzyl, and
$R^{6a}$, $R^{6b}$, and $R^{6c}$ are independently selected from the group consisting of:
(1) hydrogen,
(2) halogen,
(3) —OR$^5$,
(4) —SR$^5$, and
(5) C$_{1-6}$alkyl;
$R^7$ is selected from the group consisting of —C≡C—, O, S, and NH;
Z is selected from the group consisting of CO, CH—OH, and

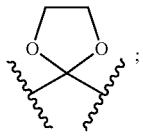

$R^{8a}$ and $R^{8b}$ are independently selected from the group consisting of:
(1) nitrile
(2) hydrogen,
(3) halogen,
(4) —OR$^5$,
(5) —SR$^5$,
(6) C$_{1-6}$alkyl,
(7) —CO$_2$R$^5$, and
(8) tetrazolyl;
$X^1$ is hydrogen and $X^2$ is hydroxyl;
n is independently 1, 2, 3, or 4;
m is independently 0, 1, or 2;
and pharmaceutically acceptable salts thereof.

2. The compound of claim 1 wherein:
$R^5$ is hydrogen or methyl;
and pharmaceutically acceptable salts thereof.

3. The compound of claim 1 wherein $R^2$ is;

$R^4$—S(O)$_2$—NR$^5$— and wherein $R^4$ is selected from the group consisting of:
(1) hydrogen,
(2) C$_{1-6}$alkyl,
(3) phenyl, and
(4) benzyl;
$R^5$ is selected from the group consisting of:
(1) C$_{1-6}$alkyl,
(2) phenyl,
(3) benzyl, and
(4) hydrogen;
and pharmaceutically acceptable salts thereof.

4. The compound of claim 1 wherein $R^3$ is:

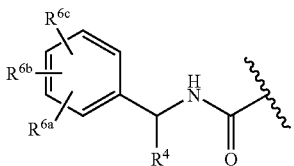

and wherein:
$R^4$ is methyl;
$R^{6a}$ is H or F;
$R^{6b}$ and $R^{6c}$ are hydrogen;
and pharmaceutically acceptable salts thereof.

5. The compound of claim 1 wherein $R^3$ is:

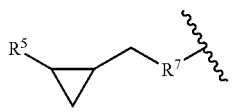

wherein:

$R^5$ is methyl;

$R^7$ is O or NH;

and pharmaceutically acceptable salts thereof.

6. The compound of claim 1 which is selected from the group consisting of:

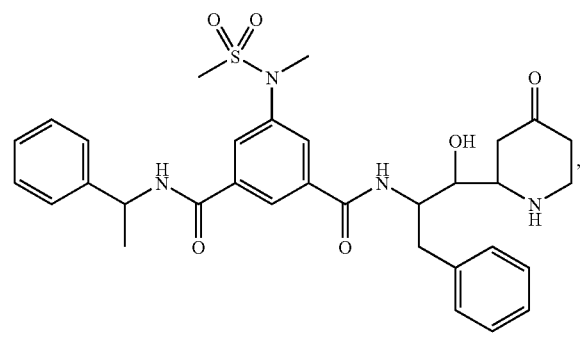

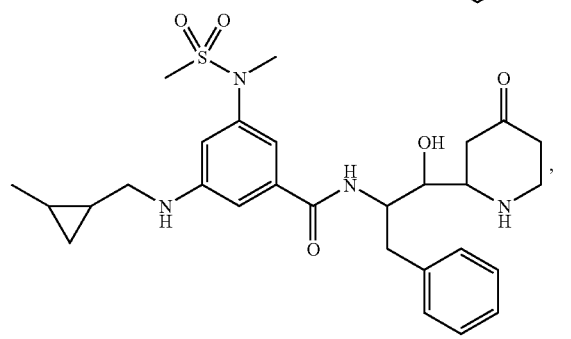

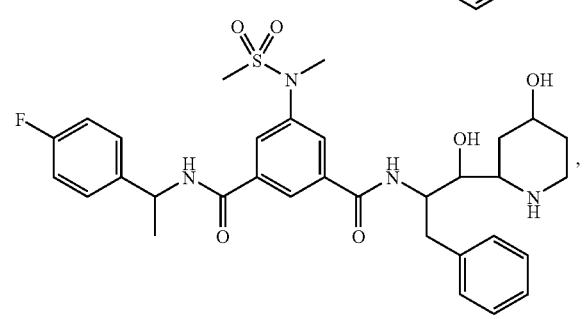

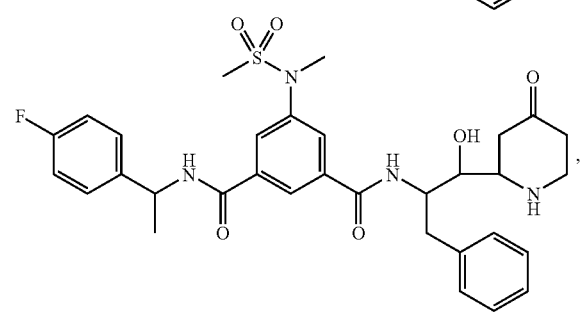

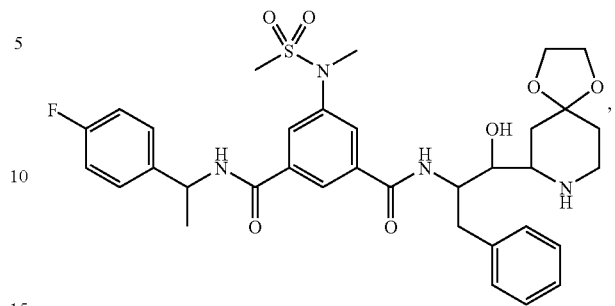

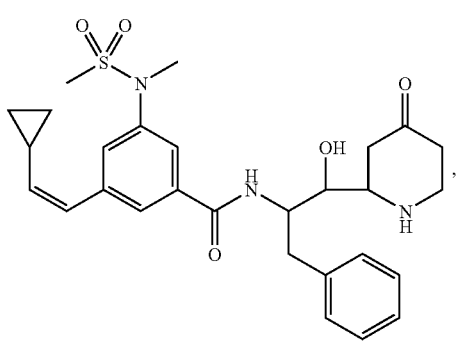

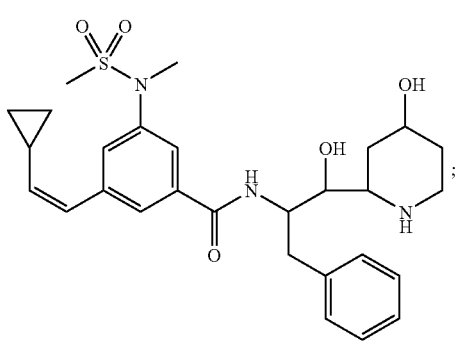

and pharmaceutically acceptable salts thereof.

7. A compound of claim 1 in substantially diastereomerically pure form.

8. A substantially diastereomerically pure compound of claim 1 in substantially enantiomerically pure form.

9. A pharmaceutical composition comprising a therapeutically effective amount of a compound of claim 1 and a pharmaceutically acceptable carrier.

10. A method for treating Alzheimer's disease in a patient comprising the administration to the patient of a therapeutically effective amount of a compound of claim 1.

* * * * *